United States Patent
Ko et al.

(10) Patent No.: US 10,568,922 B2
(45) Date of Patent: Feb. 25, 2020

(54) ANTICANCER COMPOSITION CONTAINING MIXED HERBAL MEDICINE EXTRACT AS ACTIVE INGREDIENT

(71) Applicant: UNIVERSITY-INDUSTRY COOPERATION GROUP OF KYUNG HEE UNIVERSITY, Gyeonggi-do (KR)

(72) Inventors: Seong Gyu Ko, Seoul (KR); Sung Gook Cho, Gyeonggi-do (KR); Youn Kyoung Choi, Jeju-do (KR); Hee Sun Yim, Gyeonggi-do (KR)

(73) Assignee: JAEIN RESEARCH AND PHARMACY, Seoul (KR)

( * ) Notice: Subject to any disclaimer, the term of this patent is extended or adjusted under 35 U.S.C. 154(b) by 182 days.

(21) Appl. No.: 15/882,105

(22) Filed: Jan. 29, 2018

(65) Prior Publication Data
US 2018/0169168 A1 Jun. 21, 2018

Related U.S. Application Data

(62) Division of application No. 14/897,376, filed as application No. PCT/KR2014/005116 on Jun. 11, 2014, now abandoned.

(30) Foreign Application Priority Data

Jun. 11, 2013 (KR) ........................ 10-2013-0066573

(51) Int. Cl.
| | | |
|---|---|---|
| A61K 36/481 | (2006.01) |
| A61K 36/232 | (2006.01) |
| A61K 36/428 | (2006.01) |
| A23L 33/105 | (2016.01) |
| A61K 36/258 | (2006.01) |

(52) U.S. Cl.
CPC .......... *A61K 36/481* (2013.01); *A23L 33/105* (2016.08); *A61K 36/232* (2013.01); *A61K 36/258* (2013.01); *A61K 36/428* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 6,455,078 B1 * | 9/2002 | Wu | ........................ A61K 36/00 424/725 |
| 7,901,716 B2 | 3/2011 | Kwak et al. | |
| 2002/0076446 A1 | 6/2002 | Wu | |
| 2008/0267939 A1 | 10/2008 | Oldalde et al. | |

FOREIGN PATENT DOCUMENTS

| | | |
|---|---|---|
| KR | 10-0594353 B1 | 7/2006 |
| KR | 10-2011-0049967 A | 5/2011 |
| KR | 10-2012-0122404 A | 11/2012 |
| KR | 10-2012-0124508 A | 11/2012 |
| KR | 10-2013-0036800 A | 4/2013 |

OTHER PUBLICATIONS

Akter et al., "Cytotoxic Activity Screening of Bangladeshi Medicinal Plant Extracts", J Nat Med 68: 246-252 (2013).
Cho et al., "In Vitro and In Vivo Anti-Tumor Effects of Astragalus Membranaceus", Science Direct, Cancer Letters 252, 43-54 (2007).
Heo et al., "Antiproliferative Activity of Korean Wild Vegetables on Different Human Tumor Cell Lines," Plant Foods Hum. Nutr., 2009, (64):257-263. Abstract only.
Lee et al., "In Vivo Anti-Cancer Activity of Korean Angelica Gigas and Its Major Pyranocoumarin Decursin", The American Journal of Chinese Medicine, vol. 37(1), 127-142 (2009).
SciFinder, Astragalus Membranaceus, 4 pages, Mar. 6, 2017.
Shin et al., "Trichosanthes Kirilowii Tuber Extract Induces G2/M Phase Arrest Via Inhibition of Tubulin Polymerization in HepG2 Cells", ScienceDirect, Journal of Ethnopharmacology, 115, 209-216 (2008).
Takahashi et al., "Cucurbitacin D Isolated From Trichosanthes Kirilowii Induces Apoptosis IN Human Hepatocellular Carcinoma Cells In Vitro", International Immunopharmacology, 9, 508-513 (2009).
Tseng et al., "An in Vivo Molecular Response Analysis of Colorectal Cancer Treated With Astragalus Membranaceus Extract", Oncology Reports, 35, 659-668 (2016).

* cited by examiner

*Primary Examiner* — Russell G Fiebig
(74) *Attorney, Agent, or Firm* — Christensen Fonder Dardi Herbe; Diane E. Bennett; Curtis B. Herbert

(57) ABSTRACT

The present invention relates to a composition containing, as an active ingredient, a mixed extract of *Astragalus membranaceus*, *Angelica gigas*, and *Trichosanthes kirilowii*, for preventing or treating cancer. The mixed extract of *Astragalus membranaceus*, *Angelica gigas*, and *Trichosanthes kirilowii* according to the present invention does not impact normal cell growth, while having an anticancer effect which specifically inhibits the proliferation of cancer cells, and an excellent effect of inhibiting metastasis of cancer cells, and thus can be useful in preventing or treating cancer and supplementing cancer treatment.

5 Claims, 29 Drawing Sheets

1. Non-treatment
2. Astragalus membranaceus : Angelica gigas : Trichosanthes kirilowii = 1 : 1 : 1
3. Astragalus membranaceus : Angelica gigas : Trichosanthes kirilowii = 3 : 1 : 1
4. Astragalus membranaceus : Angelica gigas : Trichosanthes kirilowii : ginseng = 1 : 1 : 1 : 1
5. Astragalus membranaceus : Angelica gigas : Trichosanthes kirilowii : ginseng = 3 : 1 : 1 : 1

ANTICANCER COMPOSITION CONTAINING MIXED HERBAL MEDICINE EXTRACT AS ACTIVE INGREDIENT

This application is a Divisional of application Ser. No. 14/897,376, filed Dec. 10, 2015, which claims priority to a National Stage Application No. PCT/KR2014/005116, filed Jun. 11, 2014, which claims priority to Korean Patent Application No. 10-2013-0066573, filed Jun. 11, 2013, which are hereby incorporated herein by reference.

FIELD OF THE INVENTION

The present invention relates to a composition including, as an active ingredient, a mixed extract of *Astragalus membranaceus*, *Angelica gigas*, and *Trichosanthes kirilowii*, for preventing or treating cancer.

BACKGROUND

Cancer is one of incurable diseases to be resolved by humanity and the huge capital has been invested in development for treating the cancer around the world. In Korea, the cancer is a first disease among causes of disease death, and more than 100,000 persons per year are diagnosed as the cancer and about more than 60,000 persons have died. A carcinogen which is the cancer initiator includes smoking, ultraviolet rays, chemicals, foods and other environmental factors, but the initiator is various and thus, it is difficult to develop medicines and effects of the medicines vary according to a generated site. Currently, since materials used as the medicines have significant toxicity and do not selectively remove only the cancer cells, it is urgently required to develop effective anticancer agents having low toxicity for treating the cancer after causing the cancer and preventing the cancer.

Meanwhile, *Astragalus membranaceus* is distributed in South Korea, Japan, Manchuria, northeastern China, and eastern Siberia, as a perennial plant of *Wisteria floribunda* for. Alba. The *Astragalus membranaceus* is often grown as a herb, and in the oriental medicine, a herb which is collected in the fall, removed with outcrops and fine roots, and dried in the sun is called *Astragalus membranaceus* of medicinal herbs. It is known that *Astragalus membranaceus* which is used as it is without removing the bark has a better efficacy. The *Astragalus membranaceus* has effects on robustness, anhidrotics, diuresis, and small boil and is prescribed for physical weakness, fatigue and boredom, and cold sweats, and the like.

*Angelica gigas* is a dried root of *Angelica gigas* which is a perennial grass belonging to Apiaceae and the taste is sweet and the nature is warm. An effect of *Angelica gigas* includes nourishing of the blood which generates the blood when the blood is insufficient, and *Angelica gigas* promotes the blood flow of coronary artery and activates generation of erythrocytes.

*Trichosanthes kirilowii* Maximowicz means a root which is removed with the cortex of perennial *Trichosanthes kirilowii* or yellow *Trichosanthes kirilowii* belonging to Cucurbitaceae. There is no smell, the taste is bitter, the nature is cold. When resin is damaged due to heat, a thirst disease, boils, and pus are treated. *Trichosanthes kirilowii* Maximowicz mainly lowers a fever of lung and stomach, generates resin, quenches the thirst, and enhances the body.

As described above, various pharmacological effects of *Astragalus membranaceus*, *Angelica gigas*, and *Trichosanthes kirilowii* are known, but an anticancer effect of the mixed extract thereof is not known at all, and there is no research thereof.

Therefore, the inventors have continued efforts to develop new anticancer agents. As a result, the inventors completed the present invention by verifying that the mixed extract of *Astragalus membranaceus*, *Angelica gigas*, and *Trichosanthes kirilowii* does not impact normal cell growth, while having an excellent effect which specifically inhibits the proliferation of cancer cells and inhibits metastasis of cancer cells.

The present invention is directed to provide a composition including, as an active ingredient, a mixed extract of *Astragalus membranaceus*, *Angelica gigas*, and *Trichosanthes kirilowii*, for preventing or treating cancer.

Further, the present invention is directed to provide a composition including, as an active ingredient, a mixed extract of *Astragalus membranaceus*, *Angelica gigas*, and *Trichosanthes kirilowii*, for supplementing anticancer treatment.

One aspect of the present invention provides a pharmaceutical composition including, as an active ingredient, a mixed extract of *Astragalus membranaceus*, *Angelica gigas*, and *Trichosanthes kirilowii*, for preventing or treating cancer.

Another aspect of the present invention provides a food composition including, as an active ingredient, a mixed extract of *Astragalus membranaceus*, *Angelica gigas*, and *Trichosanthes kirilowii*, for preventing or improving cancer.

Yet another aspect of the present invention provides a pharmaceutical composition including, as an active ingredient, a mixed extract of *Astragalus membranaceus*, *Angelica gigas*, and *Trichosanthes kirilowii*, for supplementing anticancer treatment.

Still another aspect of the present invention provides a food composition including, as an active ingredient, a mixed extract of *Astragalus membranaceus*, *Angelica gigas*, and *Trichosanthes kirilowii*, for supplementing anticancer treatment.

The mixed extract of *Astragalus membranceus*, *Angelica gigas*, and *Trichosanthes kirilowii* according to the present invention does not impact normal cell growth, while having an anticancer effect which specifically inhibits the proliferation of cancer cells, and an excellent effect of inhibiting metastasis of cancer cells, and thus can be useful in preventing or treating cancer and supplementing cancer treatment.

*kirilowii:ginseng*=3:1:1:1) of the present invention on proliferation of cancer cells according to an extractant through an MTT assay.

Figure 5:
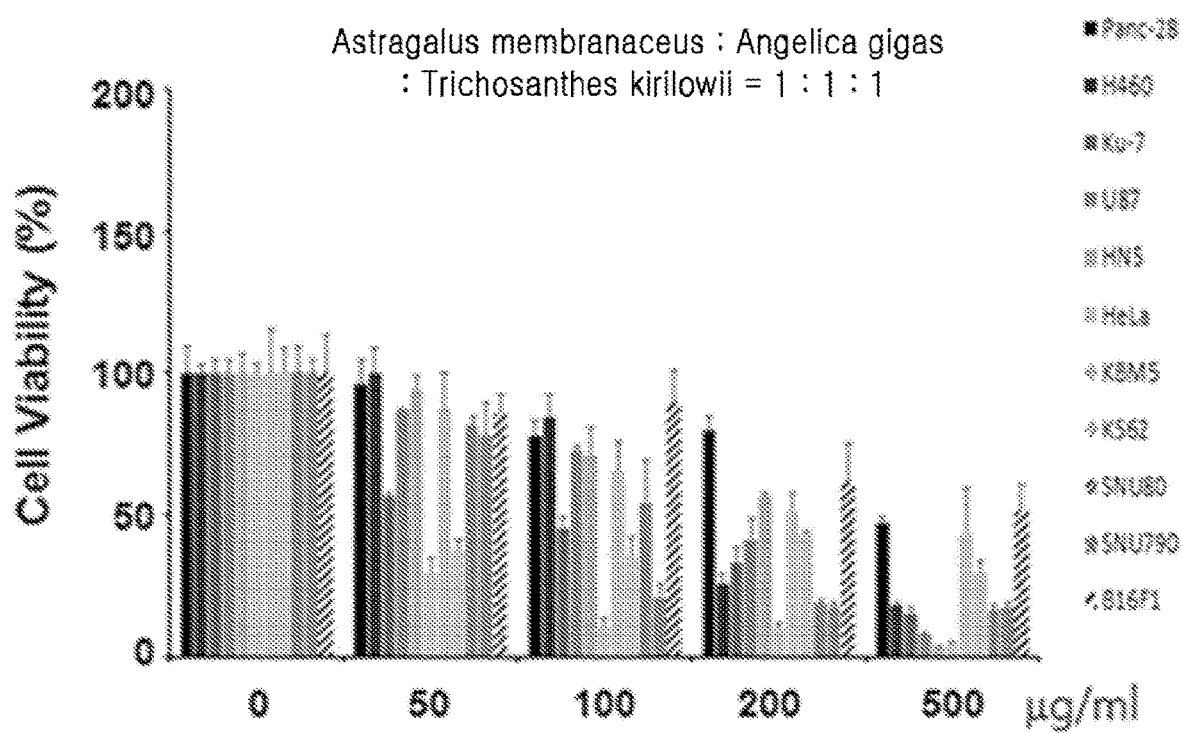

FIG. 5 is a diagram illustrating an effect of a mixed extract (*Astragalus membranaceus:Angelica gigas:Trichosanthes kirilowii*=1:1:1) of the present invention on proliferation of various kinds of cancer cells according to an extractant through an MTT assay.

Figure 6:
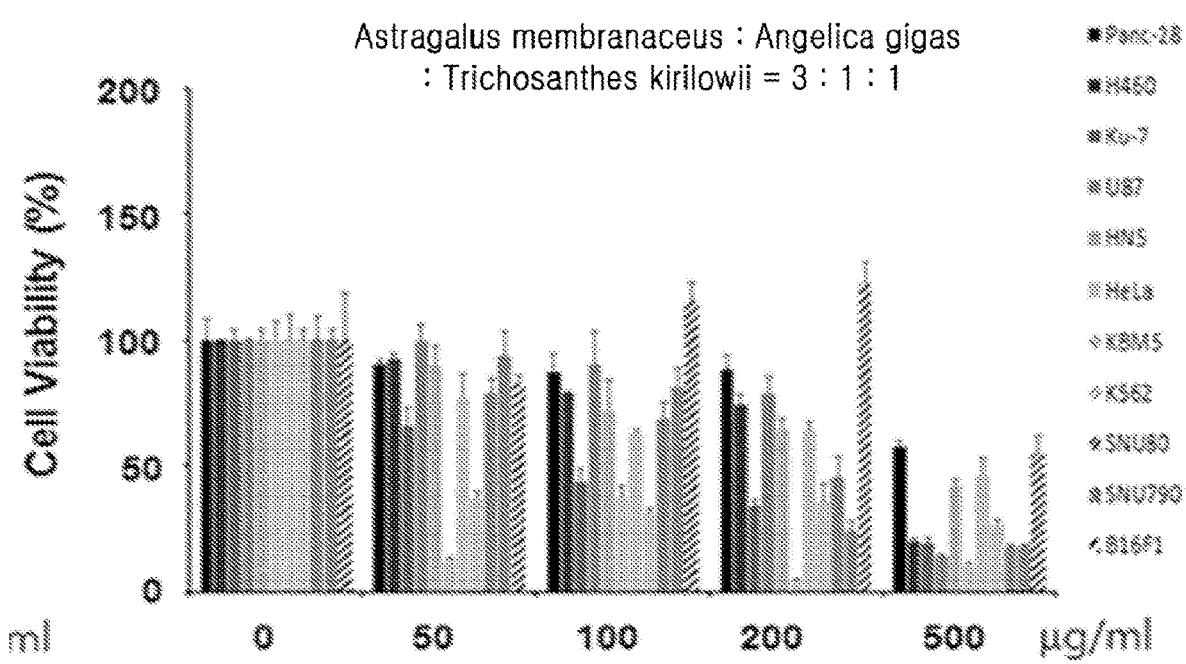

FIG. 6 is a diagram illustrating an effect of a mixed extract (*Astragalus membranaceus:Angelica gigas:Trichosanthes kirilowii*=3:1:1) of the present invention on proliferation of various kinds of cancer cells according to an extractant through an MTT assay.

Figure 7:
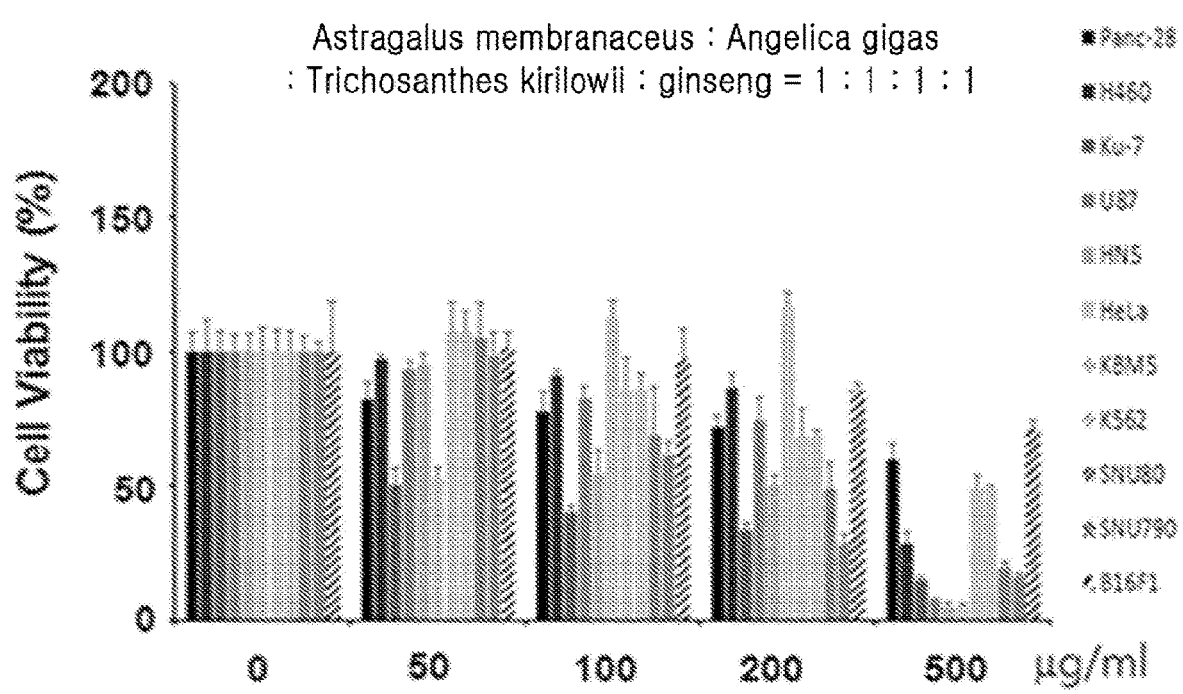

FIG. 7 is a diagram illustrating an effect of a mixed extract (*Astragalus membranaceus:Angelica gigas:Trichosanthes kirilowii:ginseng*=1:1:1:1) of the present invention on proliferation of various kinds of cancer cells according to an extractant through an MTT assay.

Figure 8:
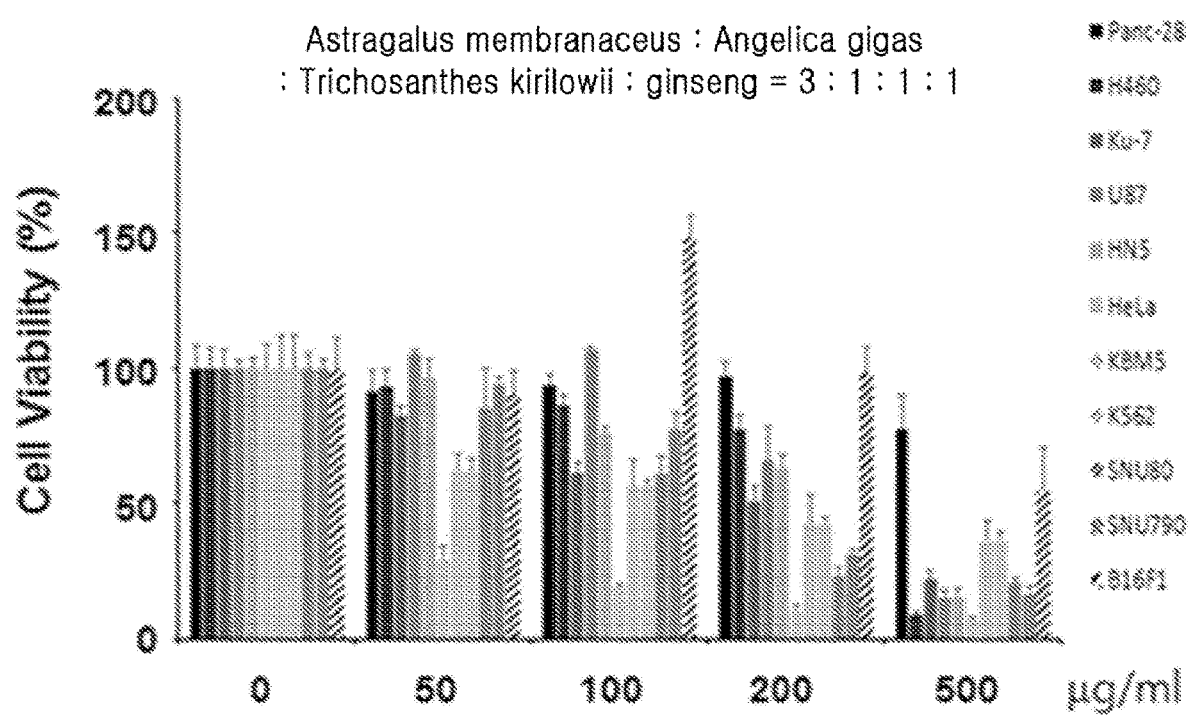

FIG. 8 is a diagram illustrating an effect of a mixed extract (*Astragalus membranaceus:Angelica gigas:Trichosanthes kirilowii:ginseng*=3:1:1:1) of the present invention on proliferation of various kinds of cancer cells according to an extractant through an MTT assay.

Figure 9:
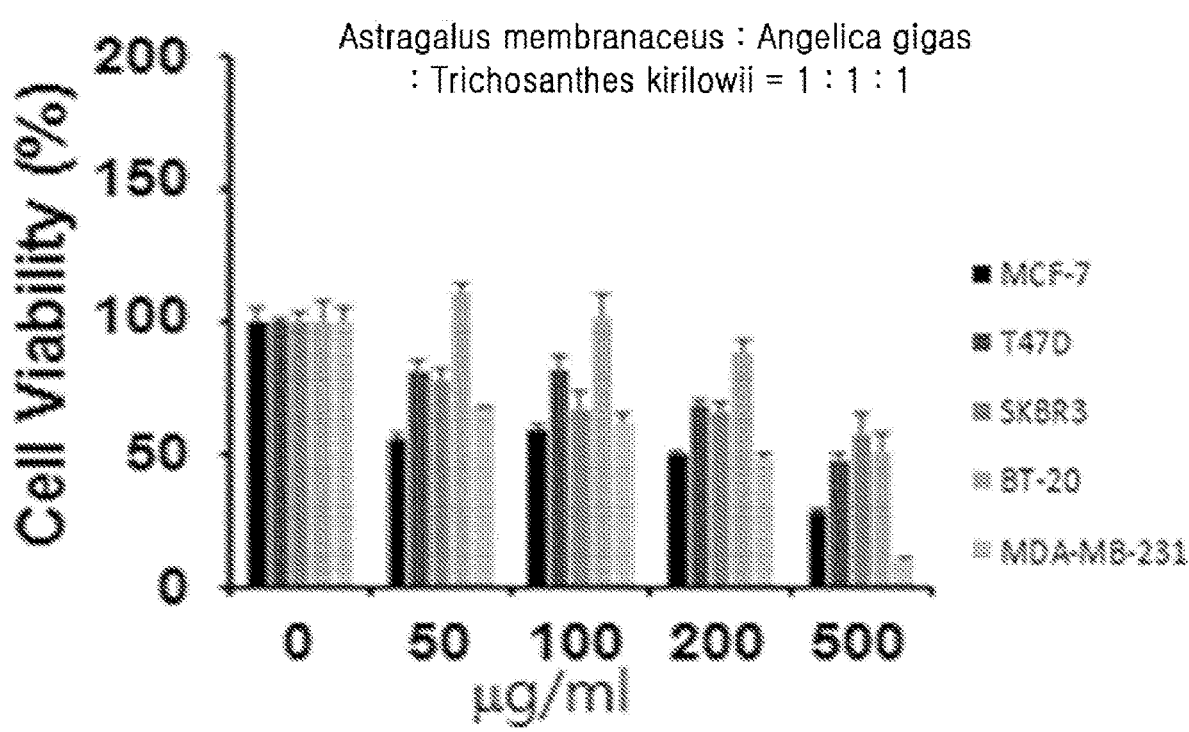

FIG. 9 is a diagram illustrating an effect of a mixed extract (*Astragalus membranaceus:Angelica gigas:Trichosanthes kirilowii*=1:1:1) of the present invention on proliferation of various kinds of breast cancer cells according to an extractant through an MTT assay.

Figure 10:
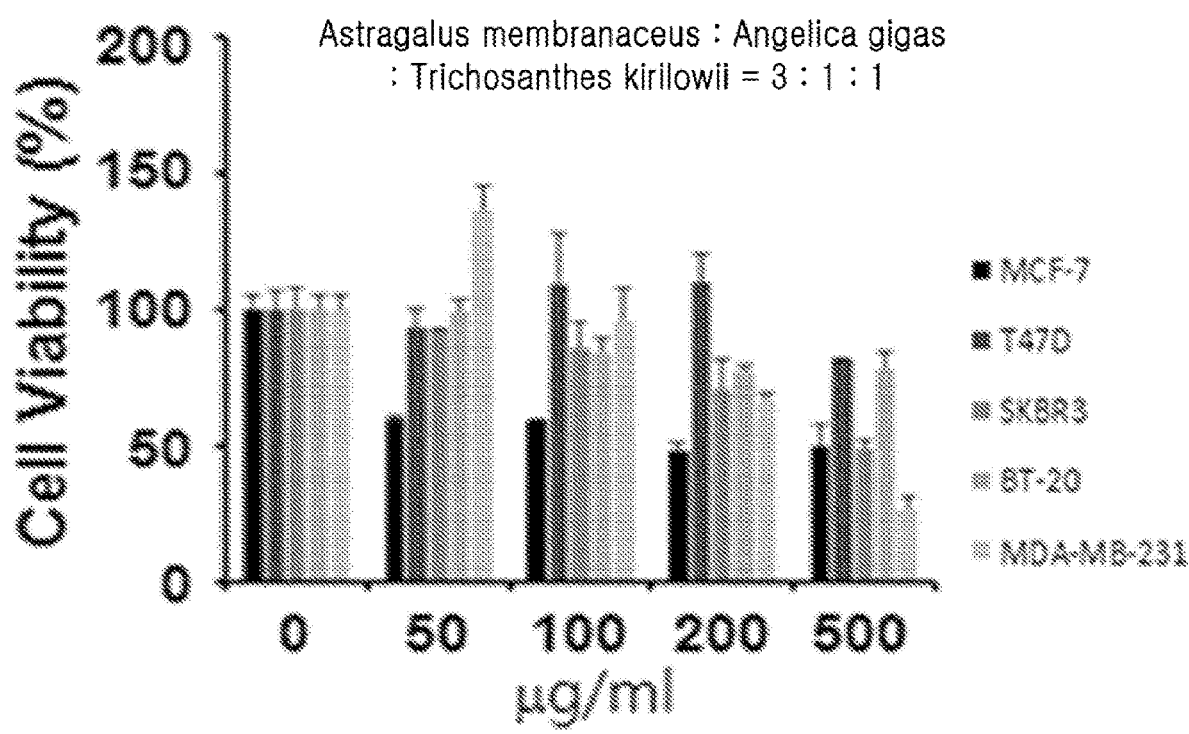

FIG. 10 is a diagram illustrating an effect of a mixed extract (*Astragalus membranaceus:Angelica gigas:Trichosanthes kirilowii*=3:1:1) of the present invention on proliferation of various kinds of breast cancer cells according to an extractant through an MTT assay.

Figure 11:
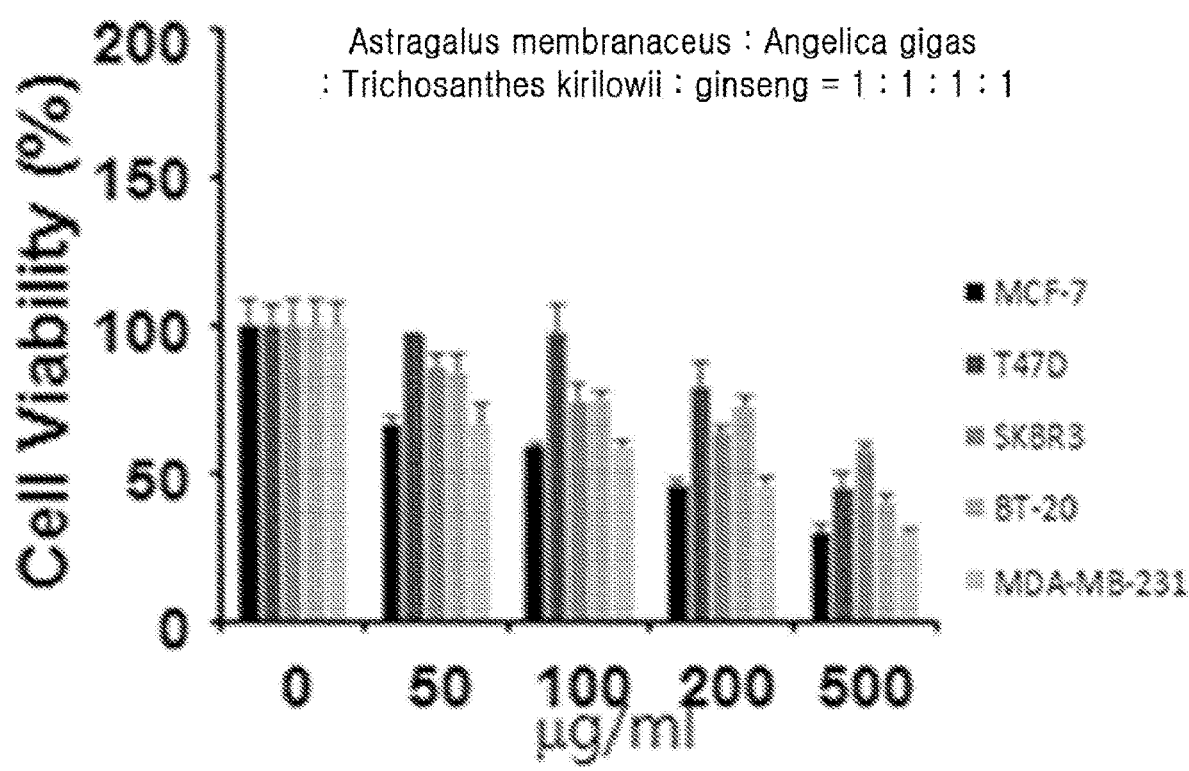

FIG. 11 is a diagram illustrating an effect of a mixed extract (*Astragalus membranaceus:Angelica gigas:Trichosanthes kirilowii:ginseng*=1:1:1:1) of the present invention on proliferation of various kinds of breast cancer cells according to an extractant through an MTT assay.

Figure 12:
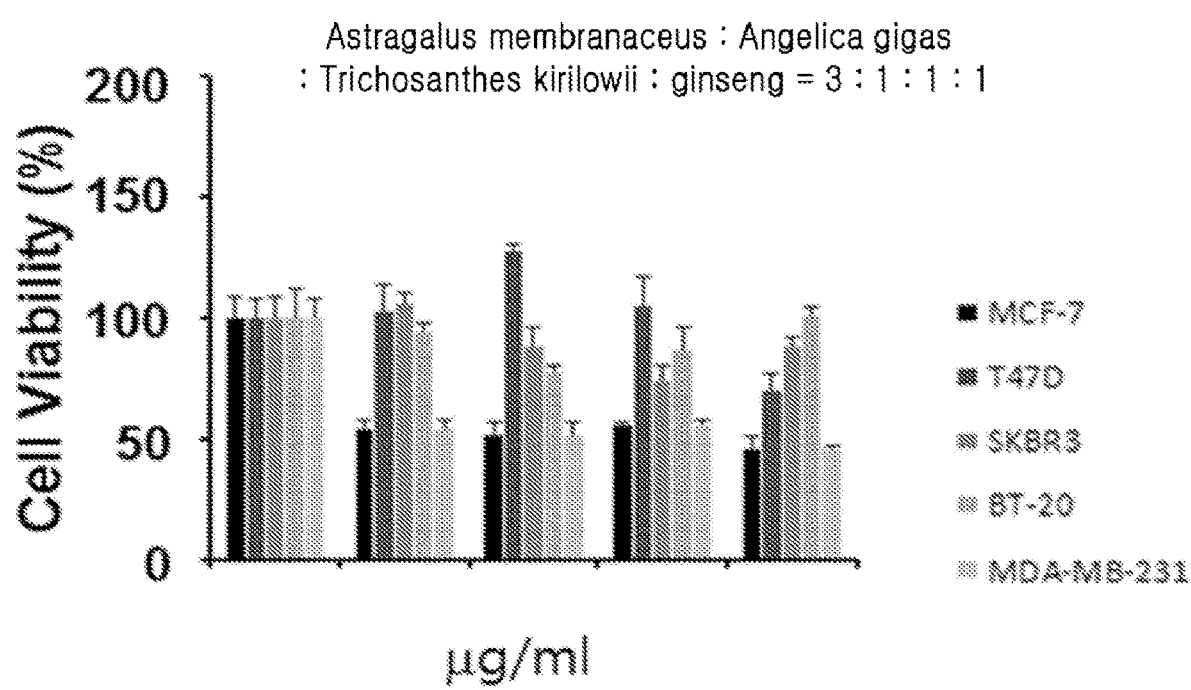

FIG. 12 is a diagram illustrating an effect of a mixed extract (*Astragalus membranaceus:Angelica gigas:Trichosanthes kirilowii:ginseng*=3:1:1:1) of the present invention on proliferation of various kinds of breast cancer cells according to an extractant through an MTT assay.

Figure 13:
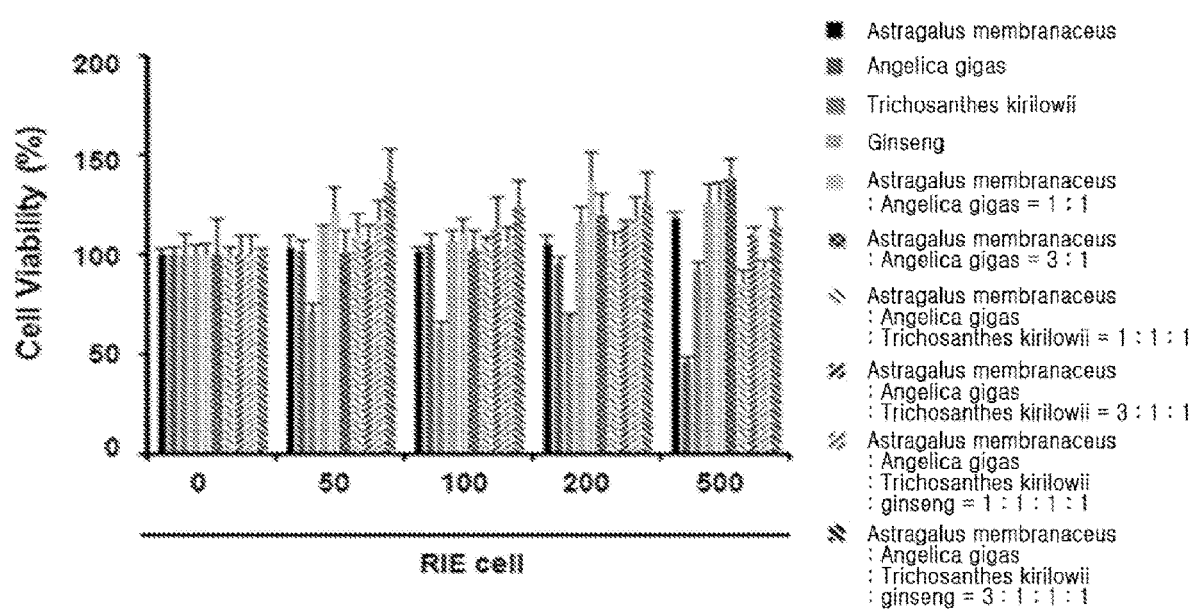

FIG. 13 is a diagram illustrating an effect of the mixed extract of the present invention on proliferation of normal cells (RIE cell) through an MTT assay.

Figure 14:
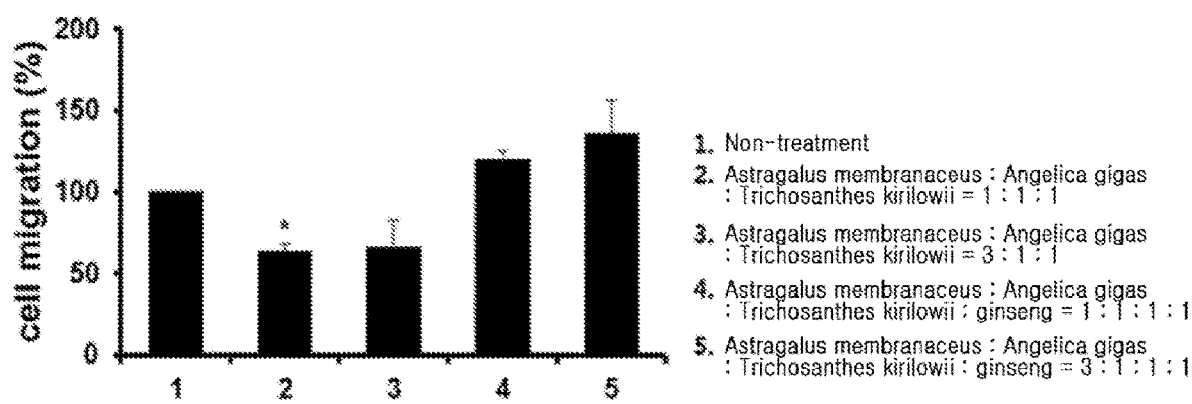

FIG. 14 is a diagram illustrating an effect of the mixed extract of the present invention on metastasis of metastatic breast cancer cells (MDA-MB-231).

Figure 15:
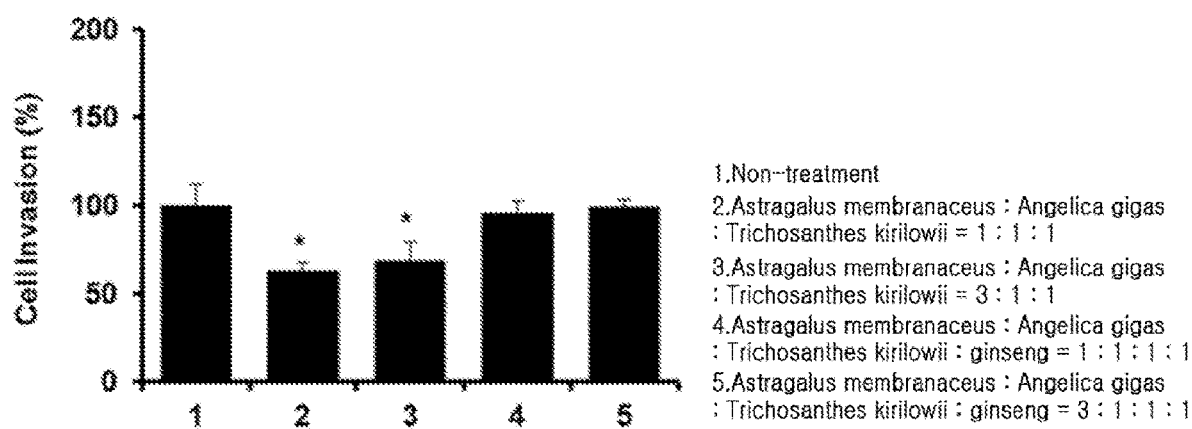

FIG. 15 is a diagram illustrating an effect of the mixed extract of the present invention on invasion of metastatic breast cancer cells (MDA-MB-231).

Figure 16:
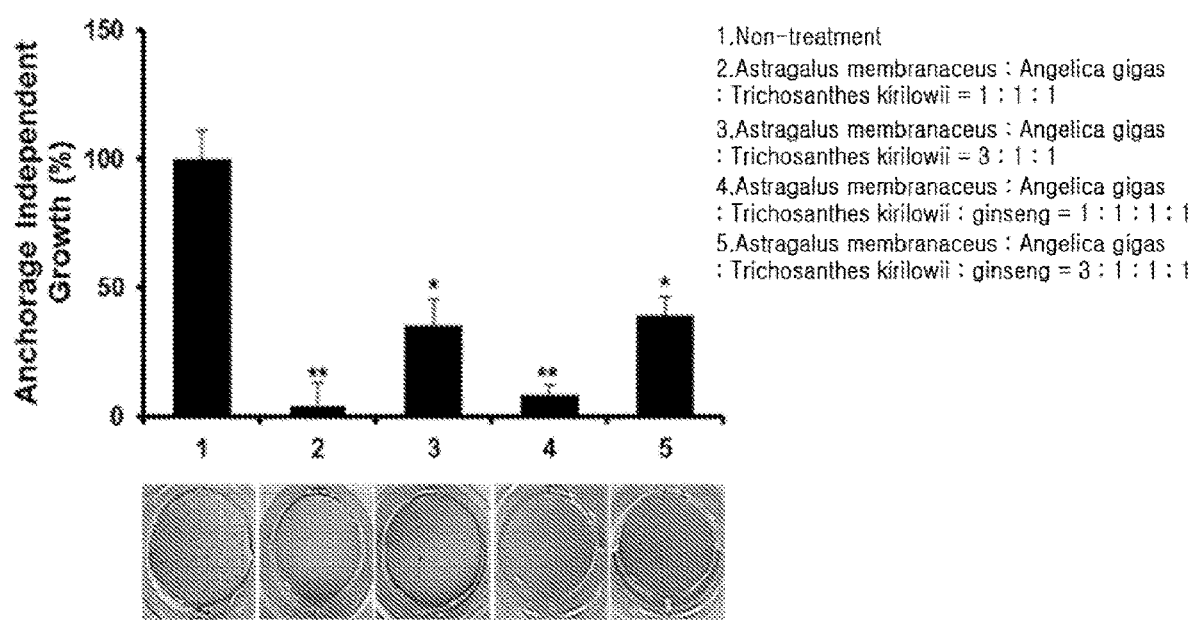

FIG. 16 is a diagram illustrating an effect of the mixed extract of the present invention on anchorage-dependence of metastatic breast cancer cells (MDA-MB-231).

Figure 17:
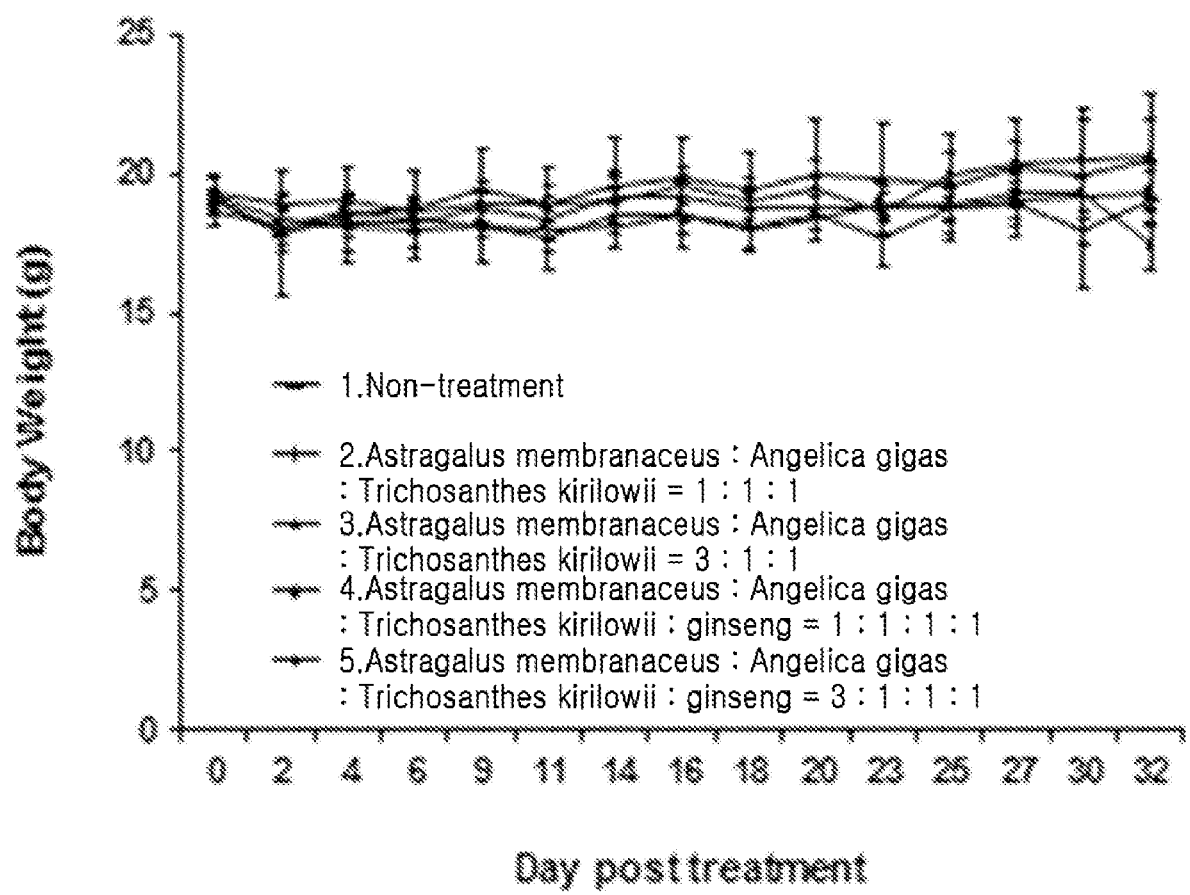

FIG. 17 is a diagram illustrating an effect of the mixed extract of the present invention on a change in weight of a mouse for an experimental period in a metastatic breast cancer animal model.

Figure 18:
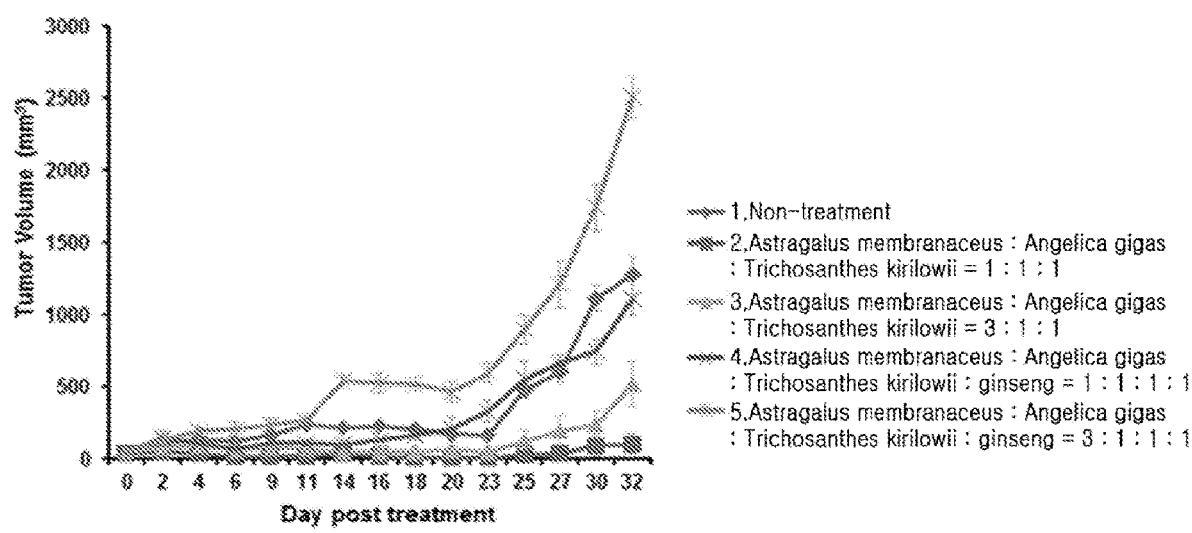
Figure 19:
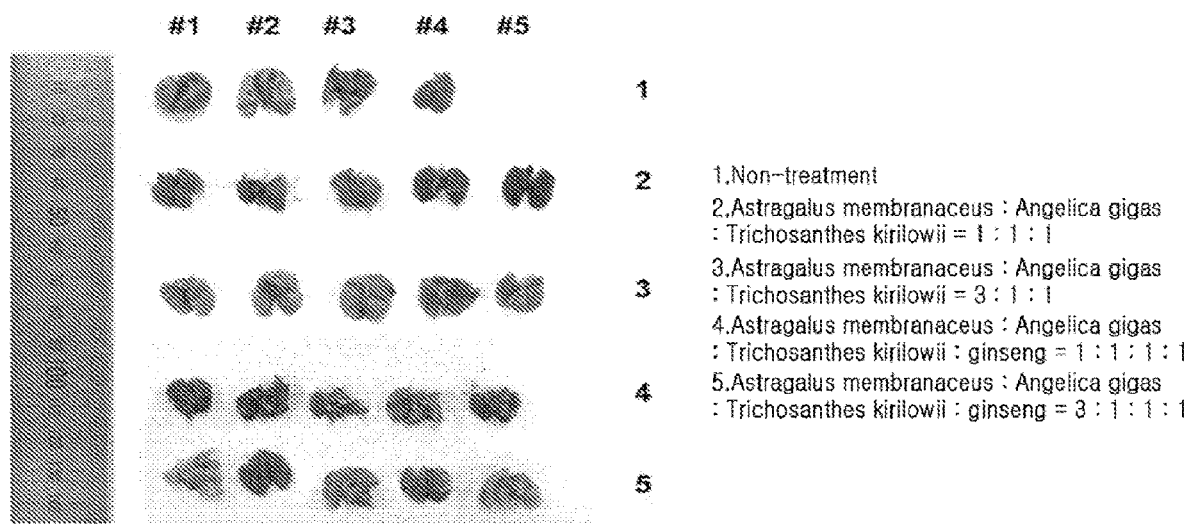

FIGS. 18 and 19 are diagrams illustrating an effect of the mixed extract of the present invention on a change in size of a cancer tissue for an experimental period in a metastatic breast cancer animal model.

Figure 20:
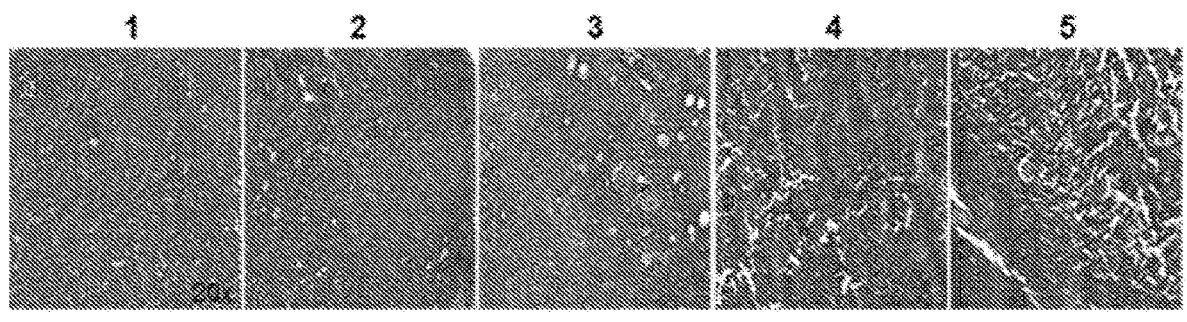

FIG. 20 is a diagram illustrating an H&E dyeing result of the cancer tissue in the metastatic breast cancer animal model.

Figure 21:
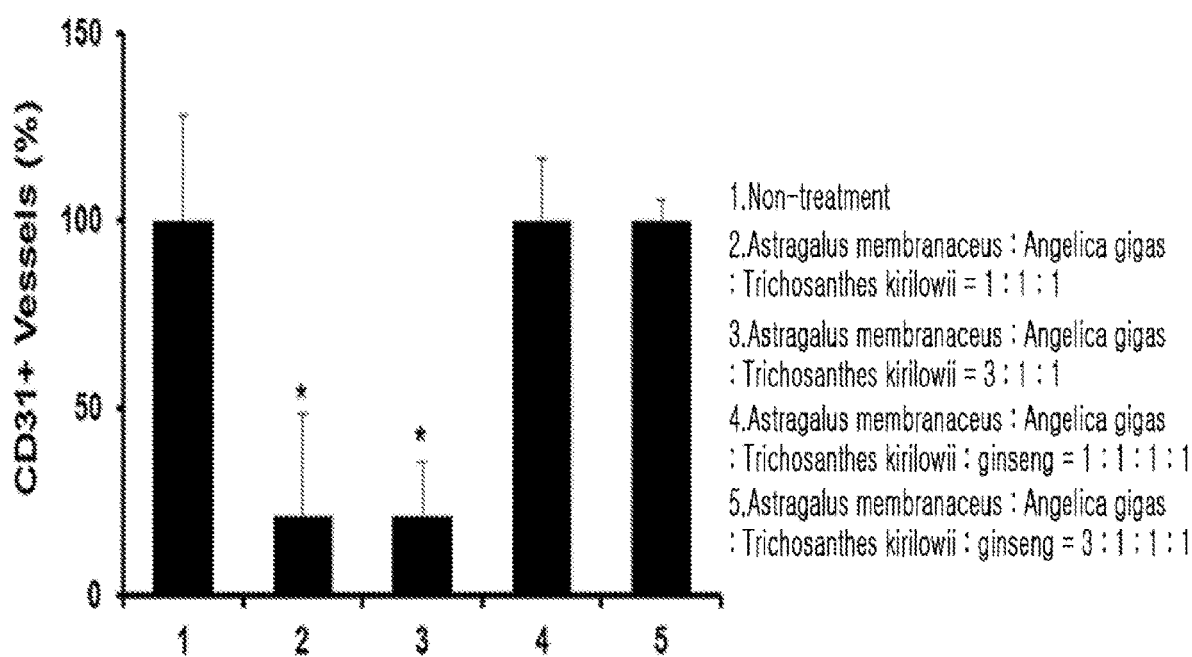

FIG. 21 is a diagram illustrating an anti-CD-31 dyeing result of the cancer tissue in the metastatic breast cancer animal model.

Figure 22:
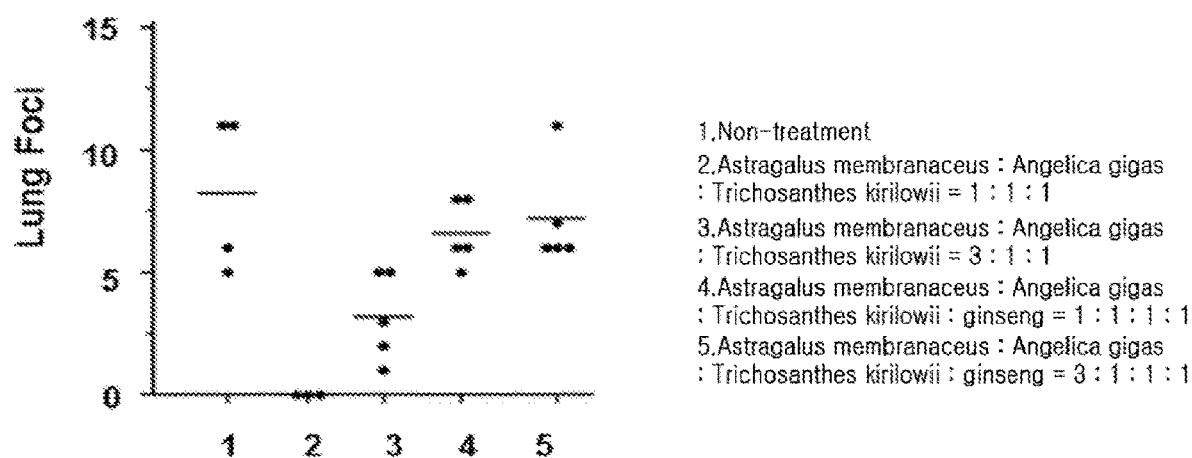

FIG. 22 is a diagram illustrating an effect of the mixed extract of the present invention on cancer metastasis in the metastatic breast cancer animal model.

Figure 23:
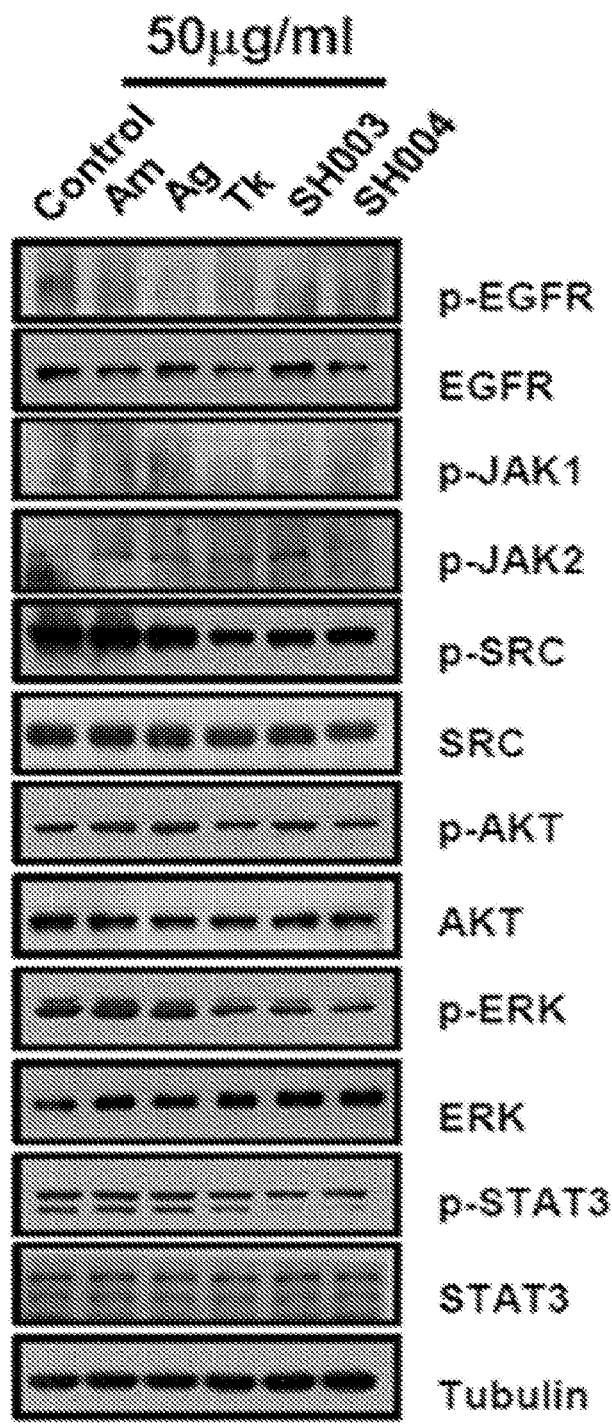
Figure 24:
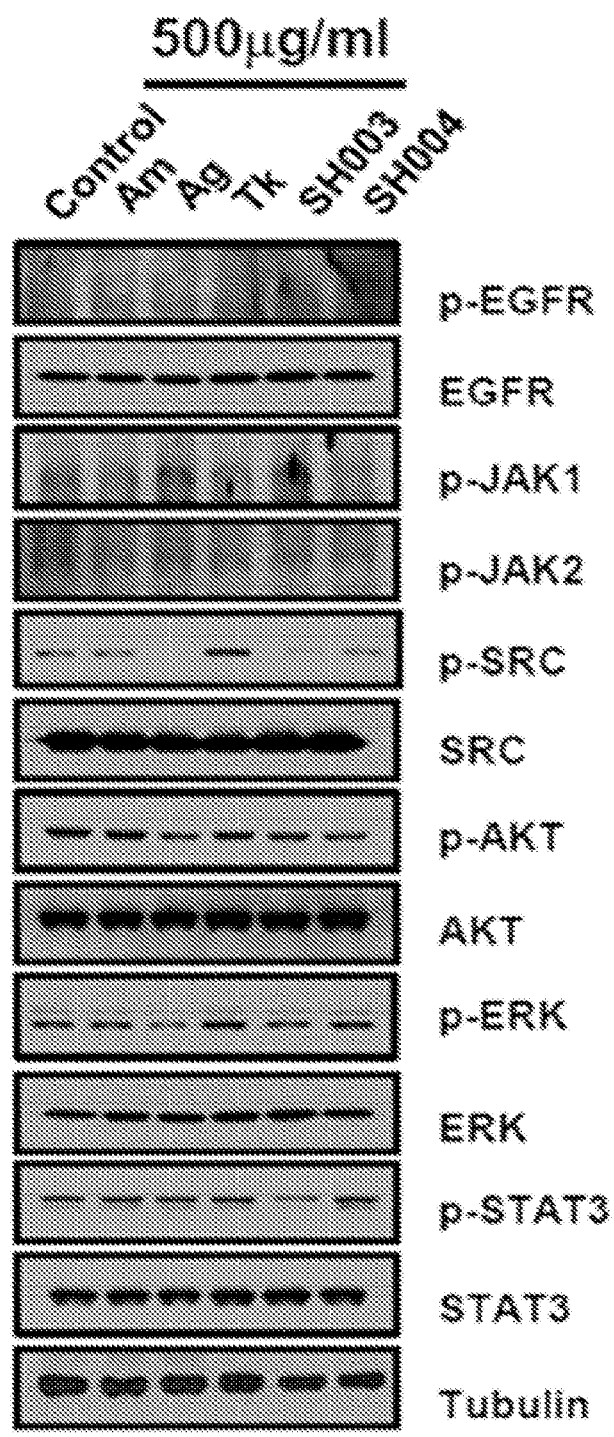

FIGS. 23 and 24 are diagrams illustrating an effect of the mixed extract of the present invention on a signal transduction system of metastatic breast cancer cells (MDA-MB-231).

Figure 25:
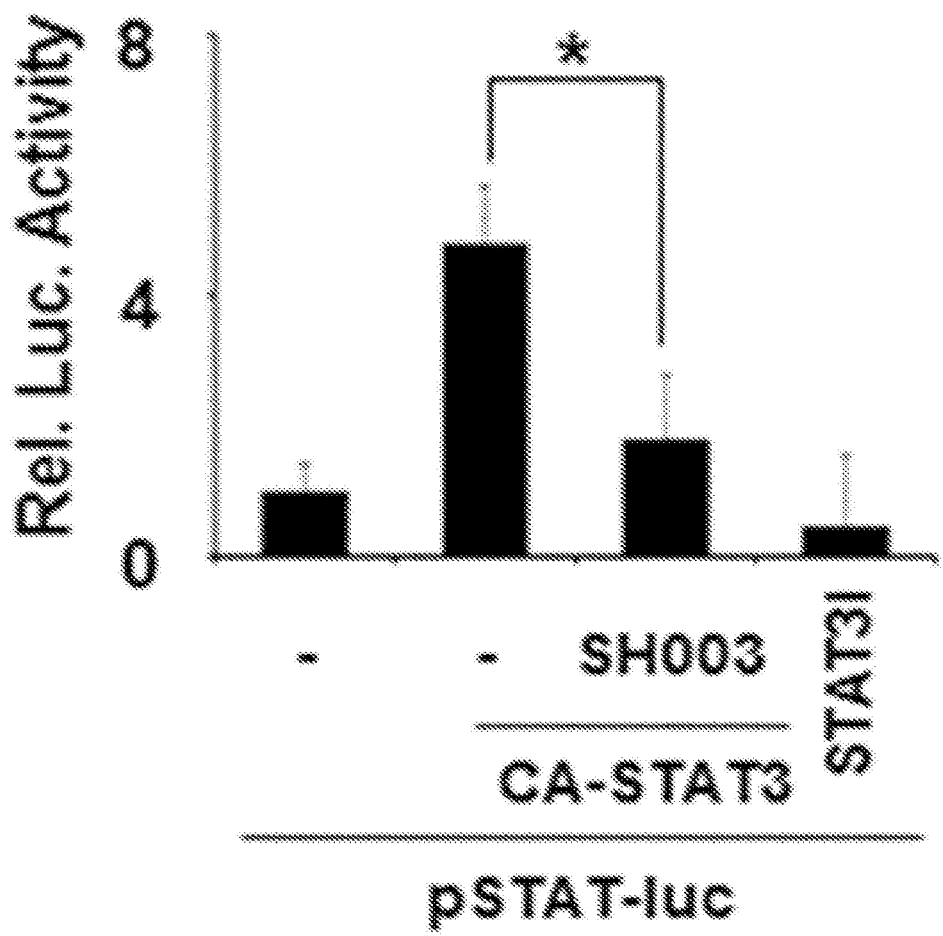

FIG. 25 is a diagram illustrating an effect of the mixed extract of the present invention on activity of a STAT3 transcription factor in 293 T cells.

Figure 26:
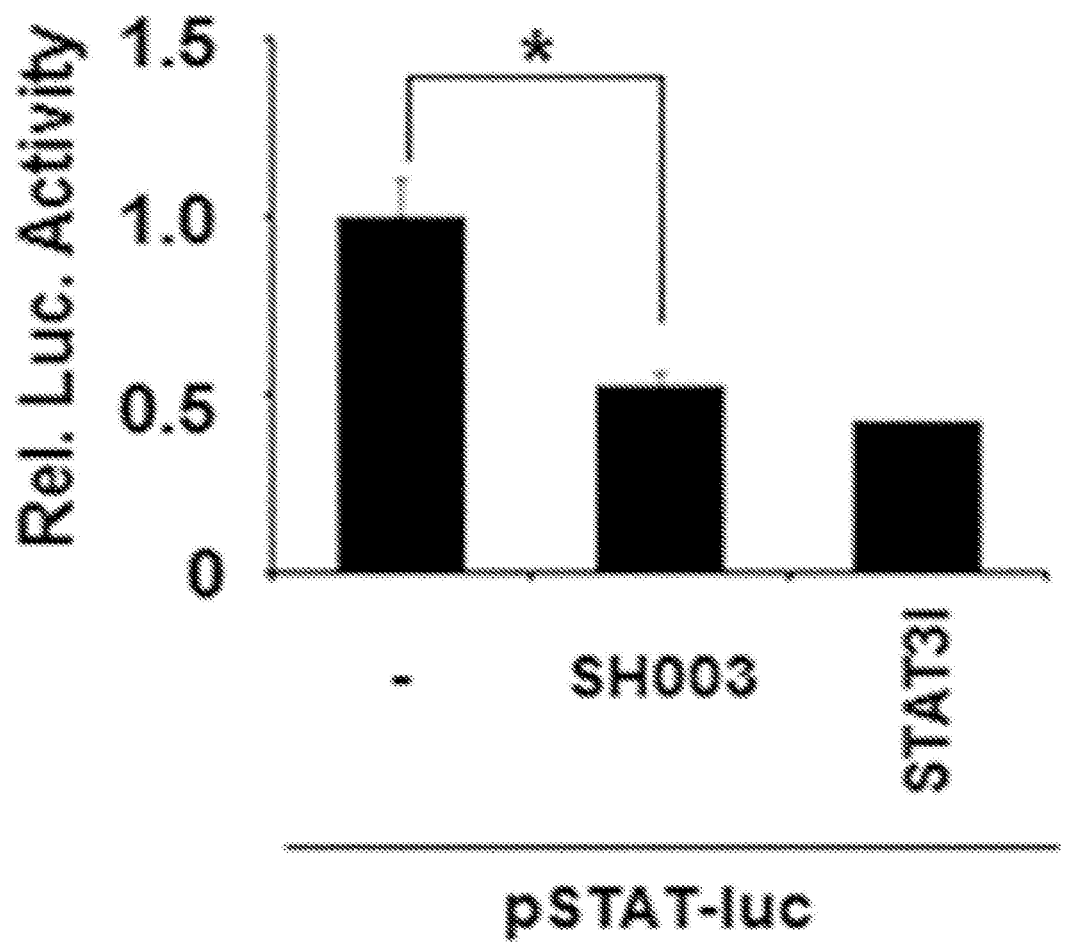

FIG. 26 is a diagram illustrating an effect of the mixed extract of the present invention on activity of a STAT3 transcription factor in metastatic breast cancer cells (MDA-MB-231).

Figure 27:
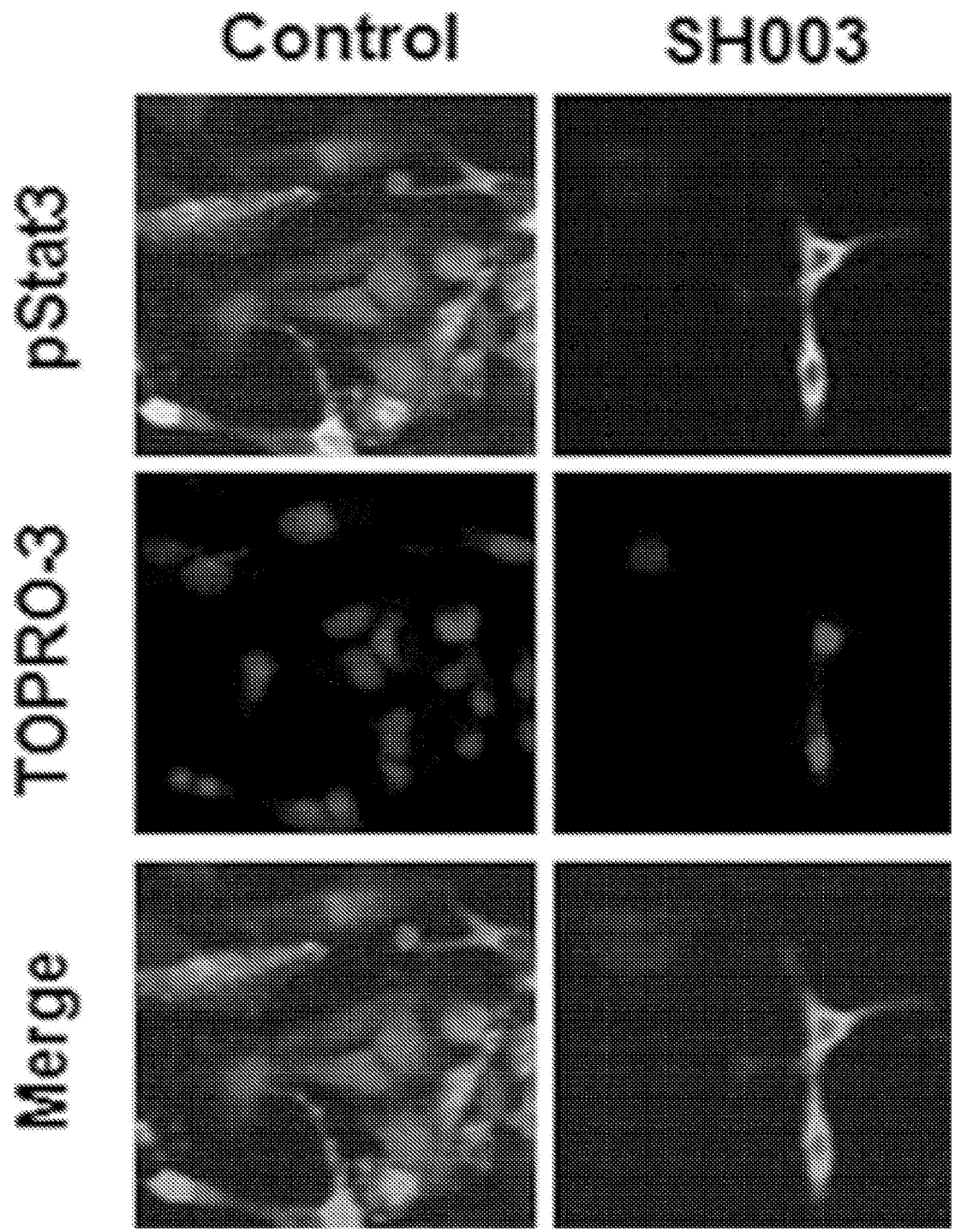

FIG. 27 is a diagram illustrating an effect of the mixed extract of the present invention on migration of STAT3 in nucleus in metastatic breast cancer cells (MDA-MB-231).

Figure 28:
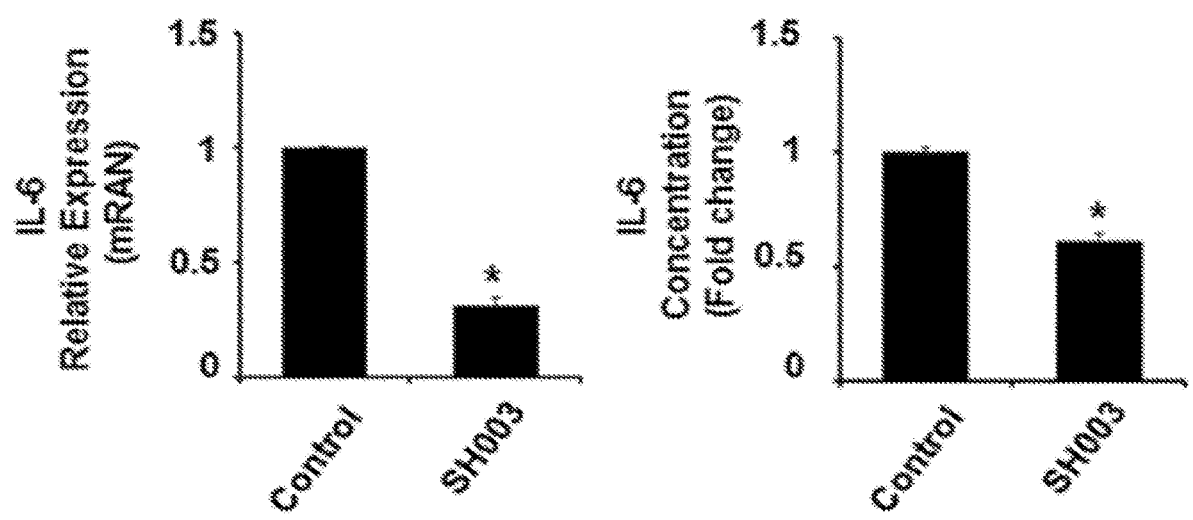

FIG. 28 is a diagram illustrating an effect of the mixed extract of the present invention on expression of IL-6 in metastatic breast cancer cells (MDA-MB-231).

Figure 29:
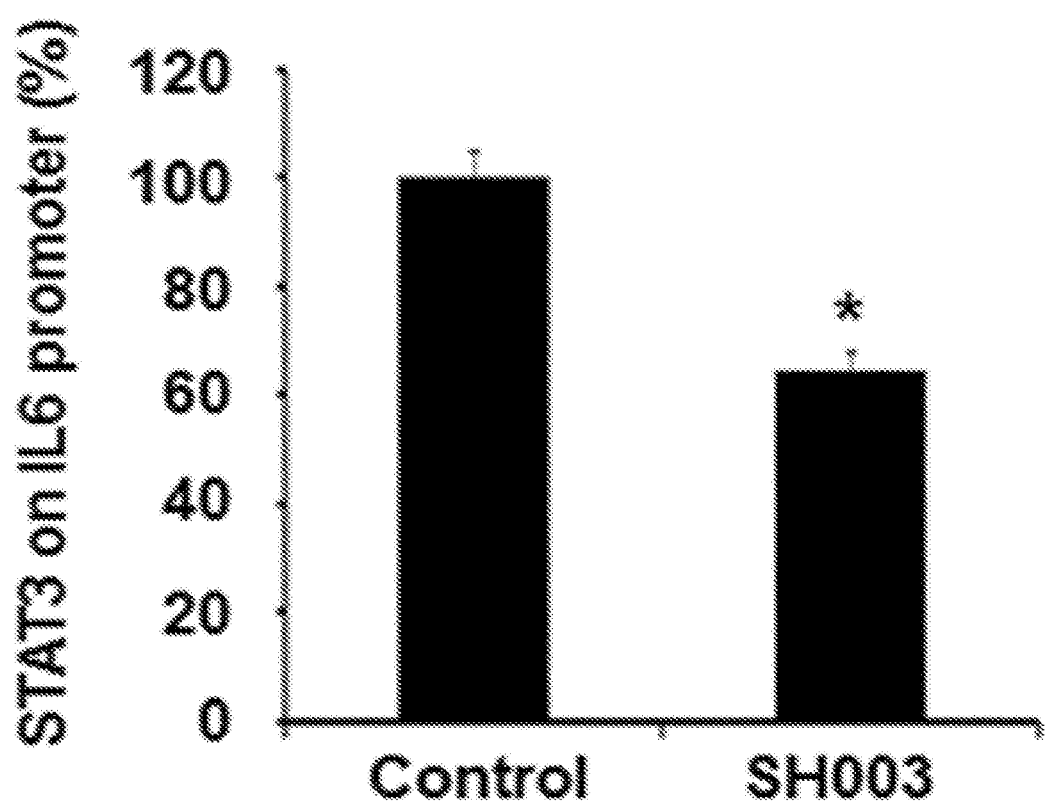

FIG. 29 is a diagram illustrating an effect of the mixed extract of the present invention on binding of an IL-6 promoter and STAT3 in metastatic breast cancer cells (MDA-MB-231).

DETAILED DESCRIPTION

Hereinafter, exemplary embodiments of the present invention will be described in detail. However, the present invention is not limited to the exemplary embodiments disclosed below, but can be implemented in various forms. The following exemplary embodiments are described in order to enable those of ordinary skill in the art to embody and practice the invention.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present invention. As used here, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined here.

The present invention provides a composition including, as an active ingredient, a mixed extract of *Astragalus membranaceus*, *Angelica gigas*, and *Trichosanthes kirilowii*, for preventing or treating cancer.

Further, the present invention provides a composition including, as an active ingredient, a mixed extract of *Astragalus membranaceus*, *Angelica gigas*, and *Trichosanthes kirilowii*, for supplementing anticancer treatment.

The composition includes a pharmaceutical composition or a food composition.

Hereinafter, the present invention will be described in more detail.

In the composition of the present invention, the mixed extract of *Astragalus membranaceus*, *Angelica gigas*, and *Trichosanthes kirilowii* as the active ingredient may be obtained by the following method.

First, *Astragalus membranaceus*, *Angelica gigas*, and *Trichosanthes kirilowii* are washed with water to remove foreign substances. *Astragalus membranaceus*, *Angelica gigas*, and *Trichosanthes kirilowii* are grown or commercialized and may be used without limitation. The *Astragalus membranaceus*, *Angelica gigas*, and *Trichosanthes kirilowii* are mixed and fully immersed by adding a solvent with a volume of 10 to 30 times. A mixed ratio of the medicinal herbs is preferably a weight ratio of *Astragalus membranaceus*:*Angelica gigas*:*Trichosanthes kirilowii*=0.5 to 5:1:1. An extractant may be immersed or heated at room temperature. The extractant is not limited thereto, but may use one or more solvents selected from water, alcohol having carbon atoms 1 to 4, and a mixed solvent thereof, preferably ethanol, and more preferably ethanol of 20 to 40% (v/v). A final mixed extract of *Astragalus membranaceus*, *Angelica gigas*, and *Trichosanthes kirilowii* is obtained by filtering and decompression-concentrating the extract.

The mixed extract may further include a *ginseng* extract. When the *ginseng* is further included, a mixed ratio of the medicinal herbs is preferably a weight ratio of *Astragalus membranaceus*:*Angelica gigas*:*Trichosanthes kirilowii*:*ginseng*=0.5 to 5:1:1:1.

The mixed extract of *Astragalus membranaceus*, *Angelica gigas*, and *Trichosanthes kirilowii* according to the present invention has an anticancer effect of specifically suppressing proliferation of only cancer cells without influencing a growth of normal cells and an excellent effect of suppressing cancer cell metastasis. As a result, the mixed extract may be advantageously used for preventing or treating cancer and supplementing anticancer treatment.

The cancer includes general cancer diseases, preferably stomach cancer, colon cancer, breast cancer, lung cancer, non-small cell lung cancer, bone cancer, pancreatic cancer, skin cancer, head cancer, neck cancer, melanoma, uterine cancer, ovarian cancer, colorectal cancer, small intestine cancer, rectal cancer, anal cancer, fallopian tube cancer, endometrial cancer, cervical cancer, vaginal cancer, vulva cancer, Hodgkin's disease, esophageal cancer, lymph node cancer, bladder cancer, gallbladder cancer, endocrine cancer, prostate cancer, adrenal cancer, soft tissue sarcoma, uterine cancer, penis cancer, chronic or acute leukemia, lymphocytic lymphoma, kidney cancer, ureter cancer, renal pelvic cancer, blood cancer, brain cancer, central nervous system (CNS) tumor, spinal cord tumor, brainstem glioma, and pituitary adenoma, more preferably breast cancer, and much more preferably metastatic breast cancer.

The composition of the present invention may further include one or more kinds of known active ingredients having an anticancer effect together with the mixed extract of *Astragalus membranaceus*, *Angelica gigas*, and *Trichosanthes kirilowii*.

The composition of the present invention may further include a carrier, an excipient, and a diluent which are properly and generally used in preparation of the pharmaceutical composition. Further, the composition of the present invention may be formulated and used in forms, such as an oral formulation such as a powder, a granule, a tablet, a capsule, a suspension, an emulsion, syrup, and an aerosol, an external preparation, a suppository, and a sterile injection solution. It is preferred that a proper medicine which is known in the art uses a medicine disclosed in the document (Remington's Pharmaceutical Science, recently, Mack Publishing Company, Easton Pa.). The carrier, the excipient, and the diluent which may be included in the composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, and the like. When the composition is formulated, the formulation may be prepared by using a diluent or an excipient, such as a filler, an extender, a binder, a wetting agent, a disintegrating agent, and a surfactant which are generally used. A solid formulation for oral administration includes a tablet, a pill, a powder, a granule, a capsule, or the like, and the solid formulation may be prepared by mixing at least one excipient, for example, starch, calcium carbonate, sucrose or lactose, gelatin, and the like with the composition. Further, lubricants such as magnesium stearate and talc may be used in addition to simple excipients. A liquid formulation for oral administration may use a suspension, a solution, an emulsion, a syrup, and the like, and may include various excipients, for example, a wetting agent, a sweetener, an aromatic agent, a preserving agent, and the like in addition to water and liquid paraffin which are commonly used as simple diluents. A formulation for parenteral administration includes a sterile aqueous solution, a non-aqueous solution, a suspension, an emulsion, and a lyophilizing agent, and a suppository. Further, as the non-aqueous solution and the suspension, propylene glycol, polyethylene glycol, a vegetable oil such as an olive oil, injectable ester such as ethyl oleate, or the like may be used. As a matter of the suppository, witepsol, macrogol, tween 61, cacao butter, laurin, glycerogelatin, and the like may be used.

The term "administration" used in the present invention means providing a predetermined composition of the present invention to an object by any proper method.

A preferable administration amount of the pharmaceutical composition of the present invention varies according to a state and a weight of the object, the degree of the disease, a drug form, and administration route and period, but may be properly selected by those skilled in the art. For a preferable effect, the mixed extract of the present invention may be administered with an amount of 1 mg/kg to 10,000 mg/kg per day and may be administered once or several times a day.

The pharmaceutical composition of the present invention may be administered to the object through various routes. Any method of administration may be expected, and for example, may be administered by oral, rectal or intravenous, intramuscular, subcutaneous, intrauterine dura mater, or cerebrovascular injection.

The composition of the present invention may be used alone or in a combination with methods using surgery, radiation therapy, hormone therapy, chemotherapy, and biological response modifiers for preventing or treating the cancer.

In the present invention, a health food means a food having a bio-modulation function such as prevention or improvement of the diseases, bio-defense, immunity, convalescent restoration, and aging suppression, and needs to be harmless to the human body when taken in the long term.

The mixed extract of *Astragalus membranaceus, Angelica gigas*, and *Trichosanthes kirilowii* of the present invention may be added to the health food for preventing or improving the cancer and supplementing anticancer treatment. When the mixed extract of *Astragalus membranaceus, Angelica gigas*, and *Trichosanthes kirilowii* of the present invention is used as food additives, the mixed extract of *Astragalus membranaceus, Angelica gigas*, and *Trichosanthes kirilowii* may be added as it is or used with other foods or food components, and may be properly used according to a general method. The mixed amount of the active ingredient may be suitably determined according to the purpose of use (prevention, health, or therapeutic treatment). Generally, the mixed extract of *Astragalus membranaceus, Angelica gigas*, and *Trichosanthes kirilowii* of the present invention is added with 15 wt % or less and preferably 10 wt % or less with respect to a raw material when preparing foods or beverages. However, in the case of long-term administration for health and hygiene or health control, the mixed extract may be added with the range or less. Since there is no problem in terms of safety, the active ingredient may be used with an amount in the range or more.

The kind of food is not particularly limited. Examples of foods which may be added with the material include meat, sausages, bread, chocolate, candies, snacks, cookies, pizza, Ramen, other noodles, gums, dairy products including ice cream, various soups, beverages, tea, drinks, alcohol drinks, and vitamin complex, and include all health foods in the ordinary acceptation.

The health beverage composition of the present invention may include various flavors, natural carbohydrates, or the like as an additional ingredient like general beverages. The natural carbohydrates may use natural sweeteners such as monosaccharides such as glucose and fructose, disaccharides such as maltose and sucrose, dextrin and cyclodextrin, synthetic sweeteners such as saccharin and aspartame, or the like. A ratio of the natural carbohydrate may be generally about 0.01 to 10 g and preferably about 0.01 to 0.1 g per 100 ml of the composition of the present invention.

The composition of the present invention may additionally include various nutrients, vitamins, electrolytes, flavoring agents, coloring agents, pectic acid and salt thereof, alginic acid and salt thereof, organic acid, a protective colloidal thickener, a pH adjusting agent, a stabilizer, a preservative, glycerin, alcohol, a carbonic acid agent used in a carbonated drink, or the like in addition to the ingredients. Besides, the composition of the present invention may include pulps for preparing natural fruit juices, fruit juice beverages, and vegetable beverages. The ingredients may be used independently or in combination. Although the ratio of the additives does not matter, generally, the ratio is selected in a range of 0.01 to 0.1 part by weight per 100 parts by weight of the composition of the present invention.

Hereinafter, preferred Examples, Experimental Examples, and Preparation Examples will be presented in order to help understanding the present invention. However, the following Examples, Experimental Examples, and Preparation Examples are just provided for more easily understanding the present invention, and the contents of the present invention are not limited by Examples, Experimental Examples, and Preparation Examples.

Example 1. Preparation of Mixed Extract of
*Astragalus membranaceus, Angelica gigas*, and
*Trichosanthes kirilowii*

*Astragalus membranaceus* (Am), *Angelica gigas* (Ag), and *Trichosanthes kirilowii* Maximowicz (Tk) were mixed with a weight ratio (w/w) of (1) 1:1:1 or (2) 3:1:1, respectively, put in an extractor, and extracted for 2 to 3 hours after adding 8 to 10 times water and 30% (v/v) ethanol or 80% ethanol, respectively. The extract was filtered and the filtrate was dried after decompression-concentrating to obtain a mixed extract (a water extract, a 30% ethanol extract, and a 80% ethanol extract) of *Astragalus membranaceus, Angelica gigas*, and *Trichosanthes kirilowii* (about 35.5% average yield of the mixed extract mixed with a weight ratio of 1:1:1 and about 29.85% average yield of the mixed extract mixed with a weight ratio of 3:1:1).

Example 2. Preparation of Mixed Extract of
*Astragalus membranaceus, Angelica gigas,
Trichosanthes kirilowii*, and *Ginseng*

*Astragalus membranaceus, Angelica gigas, Trichosanthes kirilowii* Maximowicz, and *ginseng* were mixed with a weight ratio (w/w) of (1) 1:1:1:1 or (2) 3:1:1:1, respectively, put in an extractor, and extracted for 2 to 3 hours after adding 8 to 10 times water and 30% (v/v) ethanol or 80% ethanol, respectively. The extract was filtered and the filtrate was dried after decompression-concentrating to obtain a mixed extract (a water extract, a 30% ethanol extract, and a 80% ethanol extract) of *Astragalus membranaceus, Angelica gigas, Trichosanthes kirilowii*, and *ginseng* (about 28% average yield of the mixed extract mixed with a weight ratio of 1:1:1:1 and about 24.24% average yield of the mixed extract mixed with a weight ratio of 3:1:1:1).

Experimental Example 1. Verification of Effect of Mixed Extract of the Present Invention on Growth of Cancer Cells According to Extractant In order to verify an effect of the mixed extracts prepared in Examples 1 and 2 on a growth of cancer cells according to an extractant, an MTT assay was performed by a known method in the related art. A cancer cell line used an MDA-MB-231 breast cancer cell line.

In more detail, in the MDA-MB-231 breast cancer cell line cultured on a 96-well plate, the mixed extract of *Astragalus membranaceus, Angelica gigas*, and *Trichosanthes kirilowii* or the mixed extract of *Astragalus membranaceus, Angelica gigas, Trichosanthes kirilowii*, and *ginseng* which was prepared in Examples 1 and 2 was treated with various concentrations (50 to 500 µg/ml) and then cultured for 48 hours under a condition of 37° C. and 5% $CO_2$. Thereafter, a 3-(4,5-Dimethylthiazol-2-yl)-2,5-diphenyltetrazolium bromide (MTT) reagent was treated in each cell, the cells were further cultured for 4 hours, and then a supernatant was removed and 100 µl of dimethyl sulfoxide (DMSO) was added. Finally, absorbance was measured at a wavelength of 590 nm and the absorbance value was compared with a control group which was not treated with any material. The results were illustrated in FIGS. 1 and 4.

Figure 1:
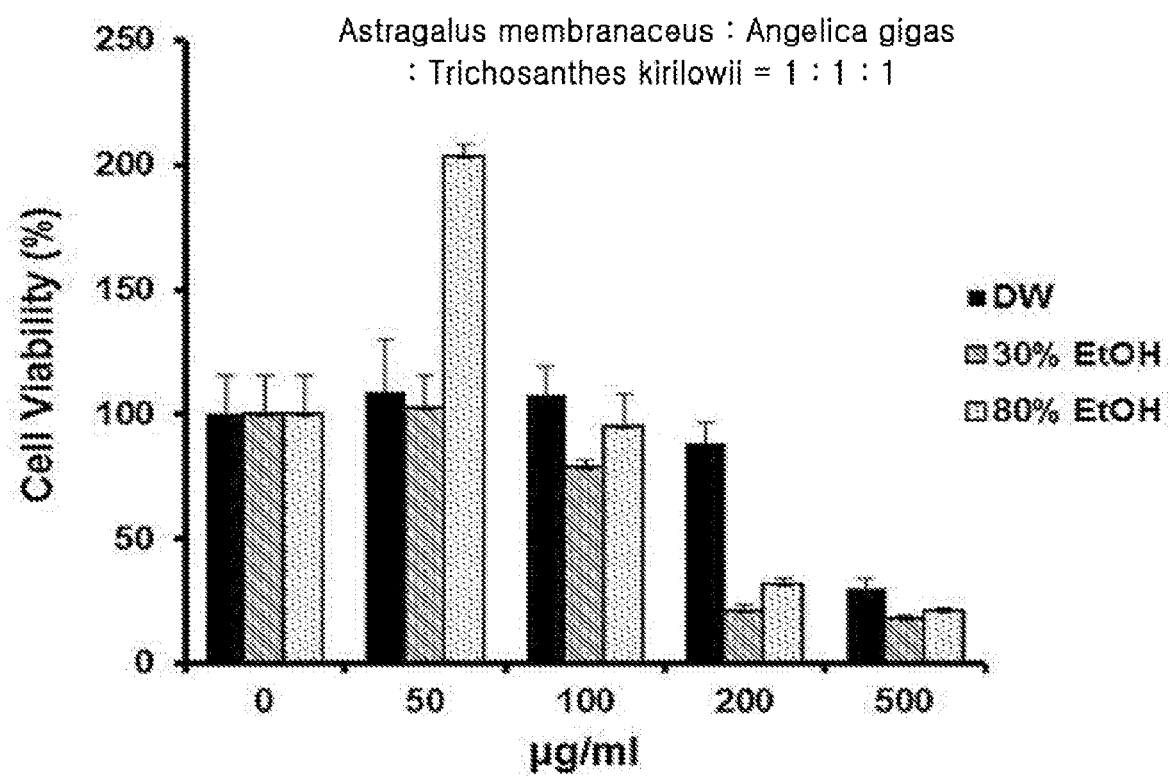
FIG. 1 is a diagram illustrating an effect of a mixed extract (*Astragalus membranaceus*:*Angelica gigas*:*Trichosanthes kirilowii*=1:1:1) of the present invention on proliferation of cancer cells according to an extractant through an MTT assay.
Figure 2:
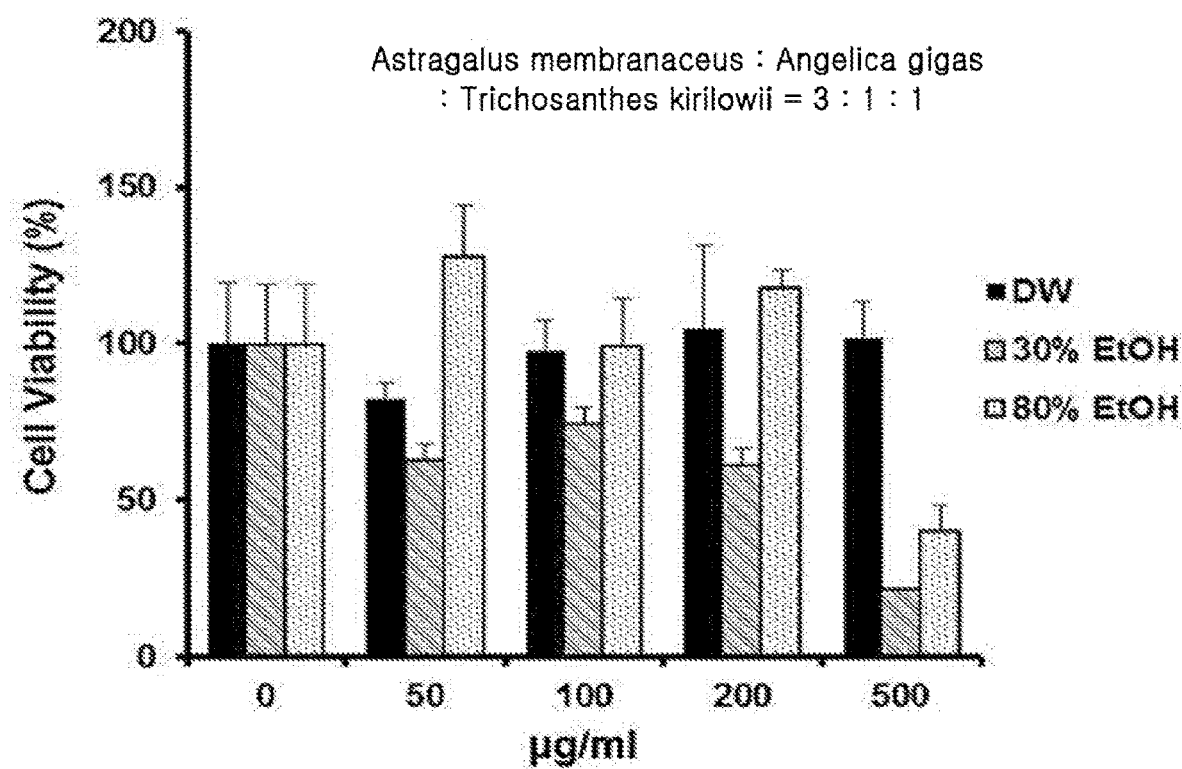
FIG. 2 is a diagram illustrating an effect of a mixed extract (*Astragalus membranaceus*:*Angelica gigas*:*Trichosanthes kirilowii*=3:1:1) of the present invention on proliferation of cancer cells according to an extractant through an MTT assay.

As illustrated in FIGS. 1 and 2, it was verified that the mixed extract of *Astragalus membranaceus, Angelica gigas*, and *Trichosanthes kirilowii* using 30% ethanol as an extractant had an excellent effect of suppressing the growth of cancer cells as compared with other solvent extracts.

Figure 3:
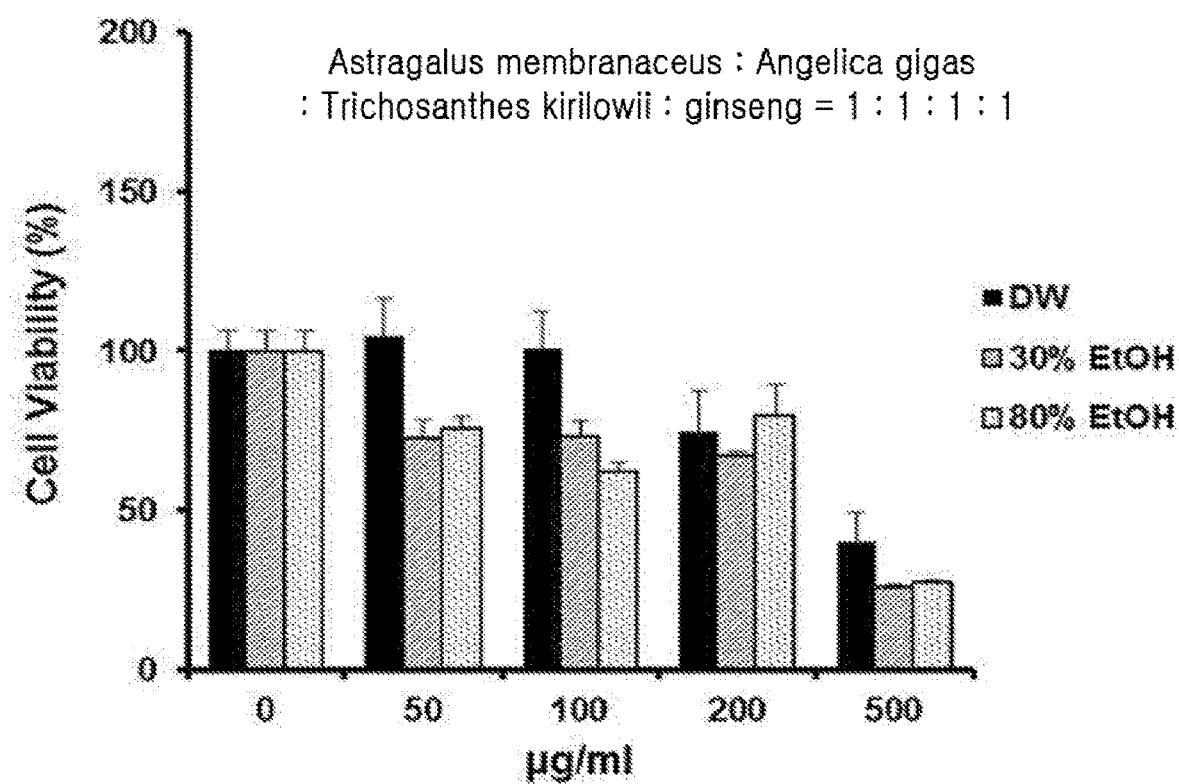
FIG. 3 is a diagram illustrating an effect of a mixed extract (*Astragalus membranaceus*:*Angelica gigas*:*Trichosanthes kirilowii*:*ginseng*=1:1:1:1) of the present invention on proliferation of cancer cells according to an extractant through an MTT assay.
Figure 4:
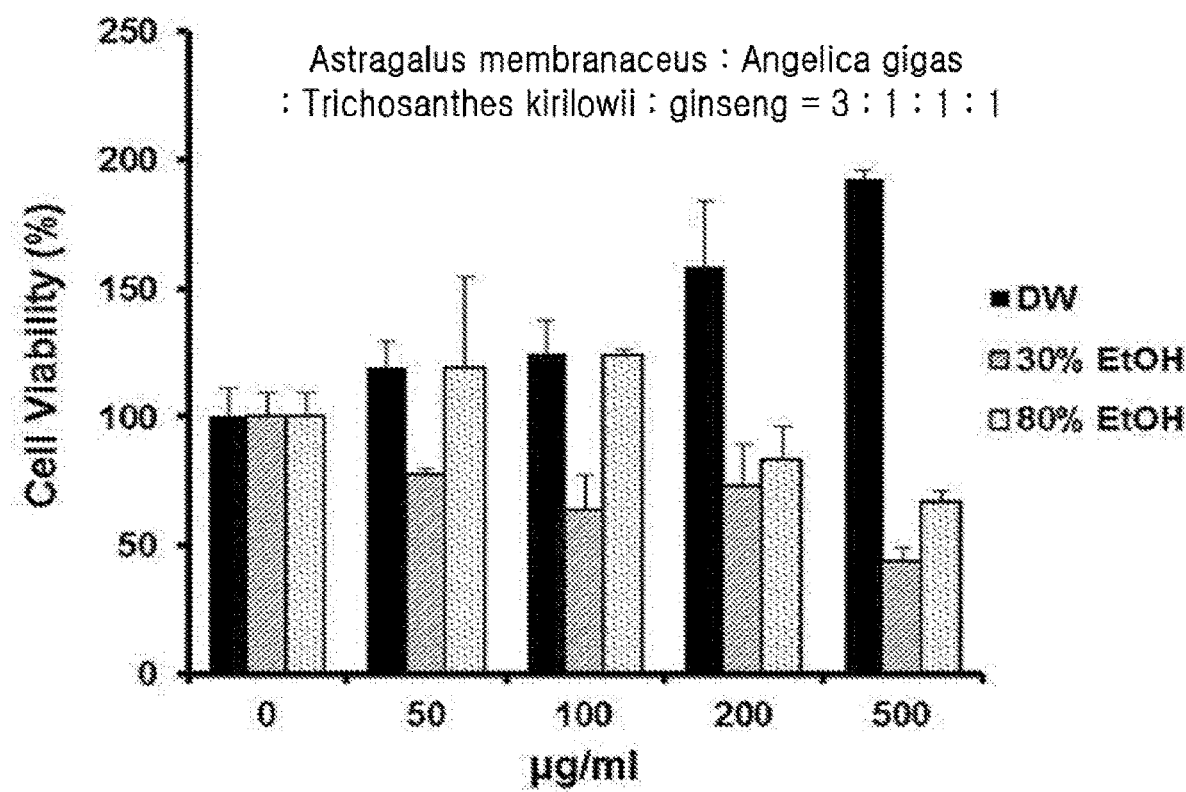
FIG. 4 is a diagram illustrating an effect of a mixed extract (*Astragalus membranaceus*:*Angelica gigas*:*Trichosanthes*

Further, as illustrated in FIGS. 3 and 4, it was verified that the mixed extract of *Astragalus membranaceus, Angelica gigas, Trichosanthes kirilowii*, and *ginseng* using 30% ethanol as an extractant had an excellent effect of suppressing the growth of cancer cells as compared with other solvent extracts.

Therefore, the following experiments used 30% ethanol extracts based on the results.

Experimental Example 2. Verification of Effect of Mixed Extract of the Present Invention on Growth of Various Cancer Cells In order to verify an effect of the mixed extracts prepared in Examples 1 and 2 on a growth of various cancer cells, the MTT assay was performed by the same method as Experimental Example 1. A cancer cell line used a pancreatic cancer cell line of Panc-28, a non-small cell lung cancer cell line of H460, a bladder cancer cell line of Ku-7, a brain tumor glioblastoma line of U87, a head and neck cancer cell line of HNS, a cervical cancer cell line of HeLa, chronic myelogenous leukemia cell lines of KBMS and K562, thyroid cancer cell lines of SNU80 and SNU790, and a skin cancer cell line B16F1. The results were illustrated in FIGS. 5 to 8.

As illustrated in FIGS. 5 and 6, it was verified that the mixed extract of *Astragalus membranaceus, Angelica gigas*, and *Trichosanthes kirilowii* had an excellent anticancer effect of suppressing the growth of various cancer cells according to a concentration.

Further, as illustrated in FIGS. 7 and 8, it was verified that the mixed extract of *Astragalus membranaceus, Angelica gigas, Trichosanthes kirilowii*, and *ginseng* also had an excellent anticancer effect of suppressing the growth of various cancer cells according to a concentration.

Experimental Example 3. Verification of Effect of Mixed Extract of the Present Invention on Growth of Various Breast Cancer Cells In order to verify an effect of the mixed extracts prepared in Examples 1 and 2 on a growth of breast cancer cells, the MTT assay was performed by the same method as Experimental Example 1. A breast cancer cell line used a total of five cell lines such as MCF-7 (hormone-positive), T47D (hormone-positive), SKBR-3 (HER-2-positive), BT-20 (TNBC, non-invasive), and MDA-MB-231 (TNBC, highly metastatic). The results were illustrated in FIGS. 9 to 12.

As illustrated in FIGS. 9 and 10, it was verified that the mixed extract of *Astragalus membranaceus, Angelica gigas*, and *Trichosanthes kirilowii* had an effect of suppressing growths of respective breast cancer cell lines according to a concentration. Particularly, it was verified that the mixed extract of *Astragalus membranaceus, Angelica gigas*, and *Trichosanthes kirilowii* which was mixed with a weight ratio of 1:1:1 had an effect of significantly suppressing the growth of MDA-MB-231 as a metastatic breast cancer cell line at a concentration of 500 µg/ml.

Further, as illustrated in FIGS. 11 and 12, it was verified that the mixed extract of *Astragalus membranaceus, Angelica gigas, Trichosanthes kirilowii*, and *ginseng* also had an effect of suppressing growths of respective breast cancer cell lines according to a concentration.

Experimental Example 4. Verification of Effect of Mixed Extract of the Present Invention on Growth of Normal Cells In order to verify that an effect of suppressing a cell growth by the mixed extract of the present invention verified through Experimental Examples 2 and 3 was cancer cell-specific, the same experiment was performed by using Rat normal intestinal epithelial cells (RIEs) as a normal cell line. The results were illustrated in FIG. 13.

As illustrated in FIG. 13, a single extract of *Astragalus membranaceus, Angelica gigas*, or *Trichosanthes kirilowii* suppressed the growth of the RIEs cells as the normal cells. On the contrary, the mixed extract of *Astragalus membranaceus, Angelica gigas*, and *Trichosanthes kirilowii* and the mixed extract of *Astragalus membranaceus, Angelica gigas, Trichosanthes kirilowii*, and *ginseng* of the present invention did not any influence the growth of the RIEs cells as the normal cells. As a result, it was verified that the mixed extract of *Astragalus membranaceus, Angelica gigas*, and *Trichosanthes kirilowii* may suppress the growth of only the specific-cancer cells by improving a negative effect of the single extract.

Experimental Example 5. Verification of Effect of Mixed Extract of the Present Invention on Metastasis of Breast Cancer Cells In order to verify an effect of the mixed extracts prepared in Examples 1 and 2 on metastasis of breast cancer cells, a scratching assay was performed by a known method in the related art. In more detail, MDA-MB-231 as a metastatic breast cancer cell line was implanted on a 6-well plate, and then cells were scraped and a distance between the cells occurred. In the cells, the mixed extract (30% ethanol extract) of *Astragalus membranaceus, Angelica gigas*, and *Trichosanthes kirilowii* or the mixed extract (30% ethanol extract) of *Astragalus membranaceus, Angelica gigas, Trichosanthes kirilowii*, and *ginseng* at a concentration of 50 µg/ml was treated and then cultured for 24 hours, and the number of moving cells was measured. The results were illustrated in FIG. 14.

As illustrated in FIG. 14, it was verified that the mixed extract of *Astragalus membranaceus, Angelica gigas*, and *Trichosanthes kirilowii* of the present invention had an effect of significantly suppressing cell migration of MDA-MB-231 as the metastatic breast cancer cell line. Particularly, it was verified that the mixed extract of *Astragalus membranaceus, Angelica gigas*, and *Trichosanthes kirilowii* which was mixed with a weight ratio of 1:1:1 had an excellent effect as compared with other extracts.

Experimental Example 6. Verification of Effect of Mixed Extract of the Present Invention on Invasion of Breast Cancer Cells In order to verify an effect of the mixed extracts prepared in Examples 1 and 2 on invasion of breast cancer cells, an invasion assay was performed by a known method in the related art. In more detail, MDA-MB-231 as the metastatic breast cancer cell line was cultured in an upper chamber precoated with matrigel and then treated with the mixed extract (30% ethanol extract) of *Astragalus membranaceus, Angelica gigas*, and *Trichosanthes kirilowii* or the mixed extract (30% ethanol extract) of *Astragalus membranaceus, Angelica gigas, Trichosanthes kirilowii*, and *ginseng* at a concentration of 50 µg/ml and then cultured for 24 hours. Invaded cells were dyed with crystal violet and the number of dyed cells was measured. The results were illustrated in FIG. 15.

As illustrated in FIG. 15, it was verified that the mixed extract of *Astragalus membranaceus, Angelica gigas*, and *Trichosanthes kirilowii* of the present invention had an effect of significantly suppressing cell invasion of MDA-MB-231 as the metastatic breast cancer cell line. Particularly, it was verified that the mixed extract of *Astragalus membranaceus, Angelica gigas*, and *Trichosanthes kirilowii* which was mixed with a weight ratio of 1:1:1 had an excellent effect as compared with other extracts.

Experimental Example 7. Verification of Effect of Mixed Extract of the Present Invention on Anchorage-Dependence of Breast Cancer Cells In order to verify an effect of the mixed extracts prepared in Examples 1 and 2 on anchorage-dependence of breast cancer cells, an anchorage-independent assay was performed by a known method in the related art. In more detail, MDA-MB-231 as the metastatic breast cancer cell line was cultured on a soft aga plate and then treated two days apart with the mixed extract (30% ethanol extract) of *Astragalus membranaceus, Angelica gigas*, and *Trichosanthes kirilowii* or the mixed extract (30% ethanol extract) of *Astragalus membranaceus, Angelica gigas, Trichosanthes kirilowii*, and *ginseng* at a concentration of 500 µg/ml and then cultured for a total of 15 days. At the fifteenth day, the cells were dyed with 0.5% crystal violet and the number of colonies was measured by using an optical microscope. The results were illustrated in FIG. 16.

As illustrated in FIG. 16, it was verified that the mixed extract of *Astragalus membranaceus, Angelica gigas*, and *Trichosanthes kirilowii* of the present invention had an effect of significantly suppressing anchorage-independent proliferation of MDA-MB-231 as the metastatic breast cancer cell line. Particularly, it was verified that the mixed extract of *Astragalus membranaceus, Angelica gigas*, and *Trichosanthes kirilowii* which was mixed with a weight ratio of 1:1:1 had an excellent effect as compared with other extracts.

Experimental Example 8. Verification of Anticancer Activity of Mixed Extract of Present Invention in Animal Model In order to verify that the mixed extract of *Astragalus membranaceus, Angelica gigas*, and *Trichosanthes kirilowii* which was prepared in Example 1 had anticancer activity in a metastatic breast cancer animal model, the following Experiment was performed. A 6-week-old nude (Nu/Nu) mouse (Oriental Science) was used as an experimental animal and MDA-MB-231 as a metastatic breast cancer cell line was subcutaneously injected into each mouse with the number of $1\times10^6$. When a cancer size was 50 mm$^3$, respective mice were randomly divided into groups. Thereafter, the mixed extract (30% ethanol extract) of *Astragalus membranaceus, Angelica gigas*, and *Trichosanthes kirilowii* or the mixed extract (30% ethanol extract) of *Astragalus membranaceus, Angelica gigas, Trichosanthes kirilowii*, and *ginseng* was orally administrated every day at a concentration of 500 mg/kg for 32 days. In a control group, water was orally administrated. A weight and a size of cancer were measured three times for a week. After the experiment ended, the mice were sacrificed, and a tissue including the cancer was separated from the mice and fixed with 4% formaldehyde. The fixed tissue was embedded with paraffin, and then for histological observation, a part thereof was dyed with hematoxylin and eosin (H & E) and in the other part, immunohistochemistry was performed by using an anti-CD31 (Abcam, Cambridge, UK) antibody. Further, in order to verify lung metastasis, the number of metastatic colonies of lung was measured. The results were illustrated in FIGS. 17 to 22.

As illustrated in FIG. 17, the mixed extract of *Astragalus membranaceus, Angelica gigas*, and *Trichosanthes kirilowii* and the mixed extract of *Astragalus membranaceus, Angelica gigas, Trichosanthes kirilowii*, and *ginseng* did not influence weights of the mice for an experimental period. As a result, it was verified that the mixed extract of the present invention was a safe material without side effects in the body.

As illustrated in FIGS. 18 and 19, it was verified that when a cancer size in the control group is 1300 mm$^3$, a cancer size in a group in which the mixed extract of *Astragalus membranaceus, Angelica gigas*, and *Trichosanthes kirilowii* which was mixed with a weight ratio of 1:1:1 was administrated was 150 mm$^3$, and a cancer size in a group in which the mixed extract which was mixed with a weight ratio of 3:1:1 was administrated was 500 mm$^3$. As a result, the mixed extract of *Astragalus membranaceus, Angelica gigas*, and *Trichosanthes kirilowii* had an excellent anticancer effect, and particularly, the mixed extract of *Astragalus membranaceus, Angelica gigas*, and *Trichosanthes kirilowii* which was mixed with a weight ratio of 1:1:1 had a more excellent anticancer effect.

As illustrated in FIG. 20, as the H&E dyed result of the cancer tissue, it was verified that in a group in which the mixed extract of *Astragalus membranaceus, Angelica gigas*, and *Trichosanthes kirilowii* was administrated, tumor cohort was well differentiated as compared with the control group.

As illustrated in FIG. 21, as a result of analyzing angiogenesis by dying the cancer tissue with the anti-CD-31 antibody, it was verified that in the group in which the mixed extract of *Astragalus membranaceus, Angelica gigas*, and *Trichosanthes kirilowii* was administrated, the number of cancer blood vessels was reduced as compared with the control group. As the result, the mixed extract of *Astragalus membranaceus, Angelica gigas*, and *Trichosanthes kirilowii* of the present invention had an excellent anticancer effect of suppressing the angiogenesis. Particularly, it was verified that the mixed extract of *Astragalus membranaceus, Angelica gigas*, and *Trichosanthes kirilowii* which was mixed with a weight ratio of 1:1:1 had a more excellent effect.

As illustrated in FIG. 22, as the result of verifying the number of metastatic colonies of lung, it was verified that in a group in which the mixed extract of *Astragalus membranaceus, Angelica gigas*, and *Trichosanthes kirilowii* was administrated, the number of lung metastatic cancer groups was significantly reduced as compared with the control group. Particularly, it was verified that the mixed extract of *Astragalus membranaceus, Angelica gigas*, and *Trichosan-*

*thes kirilowii* which was mixed with a weight ratio of 1:1:1 had a strong effect of suppressing the cancer metastasis of about 100%.

Experimental Example 9. Verification of Effect of Mixed Extract of Present Invention on Intracellular Signal Transduction System in Breast Cancer Cells In order to verify which signal transduction process the anticancer effect of the mixed extract of the present invention on the breast cancer verified in Experimental Examples 3 to 8 was caused through, the following experiment was performed.

9-1. Western Blot Analysis

Western blot was performed according to a method known in the related art. In more detail, the mixed extract (30% ethanol extract) of *Astragalus membranaceus, Angelica gigas*, and *Trichosanthes kirilowii* was treated in MDA-MB-231 as a metastatic breast cancer cell line at a concentration of 50 µg/ml or 500 µg/ml for 15 minutes (SH003: the mixed extract of *Astragalus membranaceus, Angelica gigas*, and *Trichosanthes kirilowii* which was mixed with a weight ratio of 1:1:1, and SH004: the mixed extract of *Astragalus membranaceus, Angelica gigas*, and *Trichosanthes kirilowii* which was mixed with a weight ratio of 3:1:1). Protein was separated from the cells by using an RIPA buffer solution, and then western blot was performed by using p-EGFR, EGFR, p-STAT3, STAT3, p-JAK1, p-JAK2, p-AKT, AKT antibody (hereinabove, Danvers, Mass., USA), p-SRC, SRC, p-ERK1/2, ERK1/2, or a tubulin antibody (hereinabove, Santa Cruz, Calif., USA).

As a result, amounts of proteins expressed in the cells were compared with each other. It was known that in the MDA-MB-231 as the metastatic breast cancer cell line, an intracellular signal mechanism by EGFR was very activated due to overexpression of EGFR genes or mutation. The results were illustrated in FIGS. 23 and 24.

As illustrated in FIGS. 23 and 24, it was verified that in the metastatic breast cancer cell line which was treated with the mixed extract of *Astragalus membranaceus, Angelica gigas*, and *Trichosanthes kirilowii* of the present invention, phosphorylation of EGFR and SRC and AKT which were sub signal mechanisms thereof was suppressed and phosphorylation of STAT3 which was known to be involved in development and metastasis of the cancer was suppressed.

9-2. Analysis of Effect on Activity of STAT3 Transcription Factor

In order to verify an effect of the mixed extract of the present invention on activity of a STAT3 transcription factor, the following experiment was performed.

Constitutively active STAT3 (CA-STAT3) or STAT3 siRNA in addition to STAT3-luc reporter plasmid (pSTAT3-luc) was transfected in 293 T cells and then cultured for 48 hours. Thereafter, in each cell, the mixed extract (30% ethanol extract, mixed with a weight ratio of 1:1:1, SH003) of *Astragalus membranaceus, Angelica gigas*, and *Trichosanthes kirilowii* was treated at a concentration of 50 µg/ml and further cultured for 24 hours. In each cell, transcription activity of STAT3 was measured. The results were illustrated in FIG. 25.

As illustrated in FIG. 25, it was verified that the transcription activity of STAT3 was suppressed by the mixed extract of *Astragalus membranaceus, Angelica gigas*, and *Trichosanthes kirilowii* in the 293 T cells (* $p<0.05$).

Further, pSTAT3-luc and STAT3 siRNA were transfected in the MDA-MB-231 cells in which STAT3 was abnormally activated and then cultured for 48 hours. Thereafter, in each cell, the mixed extract (30% ethanol extract, mixed with a weight ratio of 1:1:1, SH003) of *Astragalus membranaceus, Angelica gigas*, and *Trichosanthes kirilowii* was treated at a concentration of 50 µg/ml and further cultured for 24 hours. In each cell, the transcription activity of STAT3 was measured. The results were illustrated in FIG. 26.

As illustrated in FIG. 26, it was verified that the transcription activity of STAT3 was significantly suppressed by the mixed extract of *Astragalus membranaceus, Angelica gigas*, and *Trichosanthes kirilowii* in the MDA-MB-231 cells (* $p<0.05$).

9-3. Analysis of Effect on Migration in STAT3 Nucleus

In order to verify an effect of the mixed extract of the present invention on migration in STAT3 nucleus, the following experiment was performed. It was known that the activated STAT3 (pSTAT3) was migrated to a nucleus in the cell to have a transcription activity function.

In the MDA-MB-231 cell, the mixed extract (30% ethanol extract, mixed with a weight ratio of 1:1:1, SH003) of *Astragalus membranaceus, Angelica gigas*, and *Trichosanthes kirilowii* was treated for 6 hours at a concentration of 50 µg/ml and then each cell was fixed with 4% formaldehyde for 15 minutes. Thereafter, absorption of a cell membrane was promoted with 0.1% Triton X-100 and non-specific antigen-antibody binding was blocked with BSA, and then the cells were dyed with a pStat3 antibody (Cell Signaling) and TORRO-3 (Invitrogen) for 1 hour and 5 minutes and observed at 40× magnification by using a confocal microscope (Zeizz). The results were illustrated in FIG. 27.

As illustrated in FIG. 27, it was verified that STAT3 was observed only in the protoplasm, and as a result, the migration in the nucleus of STAT3 was suppressed by the mixed extract of *Astragalus membranaceus, Angelica gigas*, and *Trichosanthes kirilowii*.

9-4. Analysis of Effect on IL-6 Expression

In order to verify an effect of the mixed extract of the present invention on IL-6 expression, the following experiment was performed.

In the MDA-MB-231 cell, the mixed extract (30% ethanol extract, mixed with a weight ratio of 1:1:1, SH003) of *Astragalus membranaceus, Angelica gigas*, and *Trichosanthes kirilowii* was treated for 24 hours at a concentration of 500 µg/ml and then the expression degree of IL-6 mRNA was measured through real-time PCR and the expression degree of IL-6 protein secreted out of the cell was measured through ELISA. The results were illustrated in FIG. 28.

As illustrated in FIG. 28, it was verified that in the MDA-MB-231 cell, the mRNA expression of IL-6 as a kind of cytokine was suppressed by treating the mixed extract of *Astragalus membranaceus, Angelica gigas*, and *Trichosanthes kirilowii* and an amount of IL-6 out of the cell was reduced (* $p<0.05$).

Further, in the MDA-MB-231 cell, the mixed extract (30% ethanol extract, mixed with a weight ratio of 1:1:1, SH003) of *Astragalus membranaceus, Angelica gigas*, and *Trichosanthes kirilowii* was treated for 6 hours at a concentration of 500 µg/ml and then an amount of STAT3 bound with an IL-6 promoter was measured through a chromatin immunoprecipitation assay using EpiSeeker ChIP kit (Abcam). In more detail, in the MDA-MB-231 cell, SH003 was treated for 3 hours, and then fixed with 0.75% formaldehyde. Thereafter, DNA strands were divided through ultrasound grinding and then precipitated by using a STAT3 antibody (Cell Signaling), and the real time PCR was performed. DNA sites bound with STAT3 were amplified by using primers of 5'-GTTGTGTCTTGCCATGCTAAAG-3' and 5'-AGAATGAGCCTCAGACATCTCC-3' with −143 bp to +48 bp. The results were illustrated in FIG. 29.

As illustrated in FIG. 29, it was verified that in the MDA-MB-231 cell, the amount of STAT5 bound with the IL-6 promoter was significantly reduced by treating the mixed extract of *Astragalus membranaceus, Angelica gigas*, and *Trichosanthes kirilowii* (* p<0.05).

Hereinafter, Preparation Examples of the pharmaceutical composition and the food composition will be described, but the present invention is not limited thereto but will be described in detail.

Preparation Example 1. Preparation of Pharmaceutical Composition 1-1. Preparation of Powder
Mixed extract of *Astragalus membranaceus, Angelica gigas*, and *Trichosanthes kirilowii* 20 mg
Lactose 100 mg
Talc 10 mg
The ingredients were mixed and packed in an airtight bag to prepare the powder 1-2. Preparation of Tablet
Mixed extract of *Astragalus membranaceus, Angelica gigas*, and *Trichosanthes kirilowii* 10 mg
Corn starch 100 mg
Lactose 100 mg
Magnesium stearate 2 mg
The ingredients were mixed and tableted according to a general tablet preparing method to prepare the tablet.

1-3. Preparation of Capsule
Mixed extract of *Astragalus membranaceus, Angelica gigas*, and *Trichosanthes kirilowii* 10 mg
Crystalline cellulose 3 mg
Lactose 14.8 mg
Magnesium stearate 0.2 mg
The ingredients were mixed and filled in a gelatin capsule according to a general capsule preparing method to prepare the capsule.

1-4. Preparation of Injection
Mixed extract of *Astragalus membranaceus, Angelica gigas*, and *Trichosanthes kirilowii* 10 mg
Mannitol 180 mg
Sterile distilled water for injection 2974 mg
$Na_2HPO_4 2H_2O$ 26 mg
The injection was prepared with the content of ingredients per ampoule (2 ml) according to a general preparing method of the injection.

1-5. Preparation of Solution
Mixed extract of *Astragalus membranaceus, Angelica gigas*, and *Trichosanthes kirilowii* 20 mg
Isomerized glucose 10 g
Mannitol 5 g
Purified water Suitable amount
According to a general preparing method of the solution, respective ingredients were added in purified water and dissolved, added with a suitable amount of lemon flavoring, and mixed and then added with purified water so as to be adjusted to the entire 100 ml, and then filled in a dark amber bottle and sterilized to prepare the solution.

Preparation Example 2. Preparation of Food Composition 2-1. Preparation of Health Food
Mixed extract of *Astragalus membranaceus, Angelica gigas*, and *Trichosanthes kirilowii* 100 mg
Vitamin mixture suitable amount
Vitamin A acetate 70 μg
Vitamin E 1.0 mg
Vitamin B1 0.13 mg
Vitamin B2 0.15 mg
Vitamin B6 0.5 mg
Vitamin B12 0.2 μg
Vitamin C 10 mg
Biotin 10 μg
Nicotinamide 1.7 mg
Folic acid 50 μg
Calcium pantothenate 0.5 mg
Mineral mixture suitable amount
Ferrous sulfate 1.75 mg
Zinc oxide 0.82 mg
Magnesium carbonate 25.3 mg
First potassium phosphate 15 mg
Second potassium phosphate 55 mg
Potassium citrate 90 mg
Calcium carbonate 100 mg
Magnesium chloride 24.8 mg
A composition ratio of the mixture of vitamins and mineral was set by mixing ingredients relatively suitable for a health food, but a mixed ratio may be randomly modified. According to a general preparing method of the health food, the ingredients were mixed to prepare granules and may be used for preparing the health food composition according to a general method.

2-2. Preparation of Health Beverage
Mixed extract of *Astragalus membranaceus, Angelica gigas*, and *Trichosanthes kirilowii* 100 mg
Vitamin C 15 g
Vitamin E (powder) 100 g
Iron lactate 19.75 g
Zinc oxide 3.5 g
Nicotinamide 3.5 g
Vitamin A 0.2 g
Vitamin B1 0.25 g
Vitamin B2 0.3 g
Water required amount
According to a general preparing method of health beverage, the ingredients were mixed, stirred and heated for about 1 hour at 85° C., a prepared solution was filtrated to be obtained in a sterilized container of 2 L, sterilized after sealing, and refrigerated, and then used for preparing the health beverage composition of the present invention.

The composition ratio was set by mixing ingredients relatively suitable for a favorite beverage, but a mixed ratio may be randomly modified and implemented according to regional and national preference such as demand layers, demand countries, and a purpose of use.

The invention claimed is:
1. A method for treating breast cancer, the method comprising administering an effective amount of a mixed extract of *Astragalus membranaceus, Angelica gigas*, and *Trichosanthes kirilowii* to a subject in need thereof,
wherein the mixed extract of *Astragalus membranaceus, Angelica gigas*, and *Trichosanthes kirilowii* is prepared by mixing *Astragalus membranaceus, Angelica gigas*, and *Trichosanthes kirilowii* with a weight ratio of 1 to 3:1:1, and
wherein the mixed extract is obtained by extracting the mixture of *Astragalus membranaceus, Angelica gigas*, and *Trichosanthes kirilowii* with an extraction solvent comprising water and an alcohol having 1 to 4 carbon atoms.

2. The method of claim 1, wherein the extraction solvent is 20 to 40% (v/v) ethanol.

3. The method of claim 1, wherein the mixed extract further includes a *ginseng* extract.

4. The method of claim 3, wherein the mixed extract of *Astragalus membranaceus, Angelica gigas, Trichosanthes kirilowii*, and *ginseng* is mixed with a weight ratio of *Astragalus membranaceus:Angelica gigas:Trichosanthes kirilowii:ginseng*=0.5 to 5:1:1:1.

5. The method of claim 1, wherein the breast cancer is metastatic breast cancer.

* * * * *